US005998482A

United States Patent [19]
David et al.

[11] Patent Number: 5,998,482
[45] Date of Patent: Dec. 7, 1999

[54] USE OF SYNTHETIC POLYCATIONIC AMPHIPHILIC SUBSTANCES WITH FATTY ACID OR HYDROCARBON SUBSTITUENTS AS ANTI-SEPSIS AGENTS

[76] Inventors: Sunil A. David, 3838 Rainbow Blvd., #1209, Kansas City, Kans. 66103; David C. Morrison, 6235 Mission Dr., Mission Hills, Kans. 66208

[21] Appl. No.: 09/188,720

[22] Filed: Nov. 10, 1998

Related U.S. Application Data

[60] Provisional application No. 60/064,976, Nov. 10, 1997.

[51] Int. Cl.⁶ .................................................. A61K 31/16
[52] U.S. Cl. ............................................................ 514/626
[58] Field of Search ............................................. 514/626

[56] References Cited

U.S. PATENT DOCUMENTS

| | | | |
|---|---|---|---|
| 5,171,678 | 12/1992 | Behr et al. | 435/172.3 |
| 5,264,618 | 11/1993 | Fellgner et al. | 560/224 |
| 5,283,185 | 2/1994 | Epand et al. | 435/172.3 |
| 5,342,945 | 8/1994 | Bergeron | 544/296 |
| 5,459,127 | 10/1995 | Felgner et al. | 514/7 |
| 5,476,962 | 12/1995 | Behr et al. | 560/168 |
| 5,521,291 | 5/1996 | Curiel et al. | 530/391.7 |
| 5,527,928 | 6/1996 | Nantz et al. | 554/105 |
| 5,578,475 | 11/1996 | Jessee | 435/172.3 |
| 5,614,503 | 3/1997 | Chaudhary et al. | 514/44 |
| 5,616,745 | 4/1997 | Behr et al. | 554/56 |
| 5,627,159 | 5/1997 | Shih et al. | 514/44 |
| 5,627,266 | 5/1997 | Wainwright et al. | 530/350 |
| 5,635,380 | 6/1997 | Naftilan et al. | 435/172.3 |
| 5,635,487 | 6/1997 | Wolff et al. | 514/44 |
| 5,650,096 | 7/1997 | Harris et al. | 252/357 |
| 5,651,981 | 7/1997 | Ashley et al. | 424/450 |
| 5,658,877 | 8/1997 | Tsao | 514/2 |
| 5,661,018 | 8/1997 | Ashley et al. | 435/172.3 |

OTHER PUBLICATIONS

Feigner et al., "Lipofection: A Highly Efficient, Lipid–Mediated DNA–Transfection Procedure,"Proc. Natl. Acad. Sci. USA, 84:7413–7417.

Behr et al., "Efficient Gene Transfer Into Mammalian Primary Endocrine Cells With Lipopolyamine–Coated DNA,"Proc. Natl. Acad. Sci. USA, 86:6982–6986 (1989).

Hoess et al., "Crystal Structure of an Endotoxin–Neutralizing Protein From the Horseshoe Crab, Limulus Anti–LPS Factor, At 1.5 Å Resolution," *EMBO J.*, 12:3351–3356 (1993).

Schumann et al., "Lipopolysaccharide Binding Protein: Its Role and Therapeutical Potential in Inflammation and Sepsis," *Biochem. Soc. Trans.*, 22:80–82 (1993).

Takada et al., "Binding of Lysozyme to Lipopolsaccharide Suppresses Tumor Necrosis Factor Production In Vivo," *Infect. Immun.*, 62:1171–1175 (1994).

Behr, "Gene Transfer With Synthetic Cationic Amphiphiles: Prospects for Gene Therapy," *Bioconjug. Chem.*, 5:382–389 (1994).

David et al., "Interaction of Cationic Amphiphilic Drugs With Lipid A: Implications for Development of Endotoxin Antagonists," *Biochem. Biophys. Acta Lipids Lipid Metab.*, 1212:167–175 (1994).

(List continued on next page.)

*Primary Examiner*—Raymond Henley, III
*Attorney, Agent, or Firm*—Sonnenschein Nath & Rosenthal

[57] ABSTRACT

The present invention describes the ability of synthetic cationic amphiphilic molecules to bind and sequester bacterial lipopolysaccharides and other microbial products that share structural and/or physical-chemical properties with those of LPS. Such cationic amphiphilic molecules have a molecular structure comprised of a linear or branched backbone derived from polymethylenes or alkylamines which bear at the termini two or more protonatable positively charged groups derived from primary-amino. imidazolinium, or N, N'-unsubstituted amidinium or guanidium functions. They also possess one or more lipophilic groups derived from fatty acids or hydrocarbon substituents, attached to the backbone via amide, ester, carbamate, or urethane linkages. The use of these compounds provide low cost, effective therapeutic method for the treatment of sepsis and septic shock.

28 Claims, 10 Drawing Sheets

OTHER PUBLICATIONS

Evans et al., "Protective Effects of a Recombinant Amino–Terminal Fragment of Human Bactericidal/Permeability–Increasing Protein in an Animal Model of Gram–Negative Sepsis," *J. Infect. Dis.*, 171:153–160 (1995).

Tsukamoto et al., "Gene Transfer and Expression in Progeny After Intravenous DNA Injection Into Pregnant Mice," *Nat. Genet.*, 9:243–248 (1995).

David et al., "Interaction of Linear Dicationic Molecules With Lipid A: Structural Requisites for Optimal Binding Affinity," *J. Endotoxin. Res.*, 2:325–336 (1995).

Gao et al., "Cationic Liposome–Mediated Gene Transfer," *Gene Ther.*, 2:710–722 (1995).

Solodin et al., "A Novel Series of Amphiphilic Imidazolinium Compounds for in Vitro and in Vivo Gene Delivery," *Biochemistry*, 34:13537–13544 (1995).

Köhler et al., "Annexin V Interaction With Phosphatidylserine–Containing Vesicles at Low and Neutral pH," *Biochemistry*, 36:8189–8194 (1997).

David et al., "Lipopolyamines: Novel Antiendotoxin Compounds That Reduce Mortality in Experimental Sepsis Caused by Gram–Nagative Bacteria," *Antimicrob. Agents Chemother.*, In Press (Apr. Issue; vol. 43, #4) (1999).

Figure 2
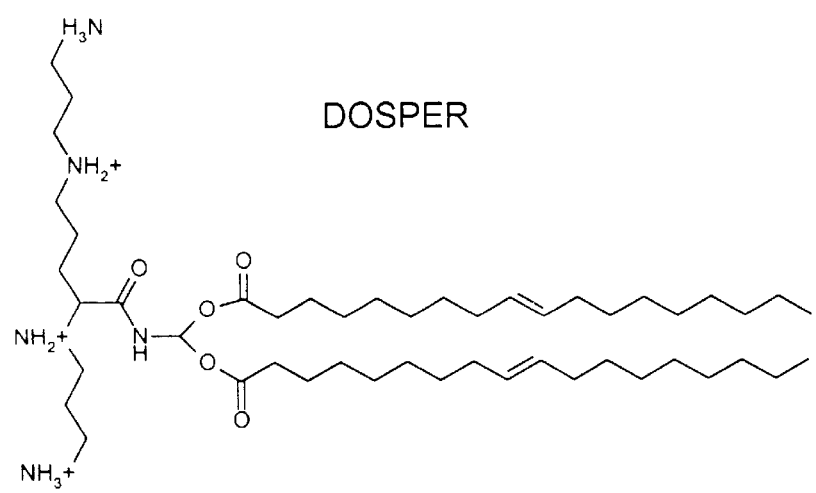
DOSPER
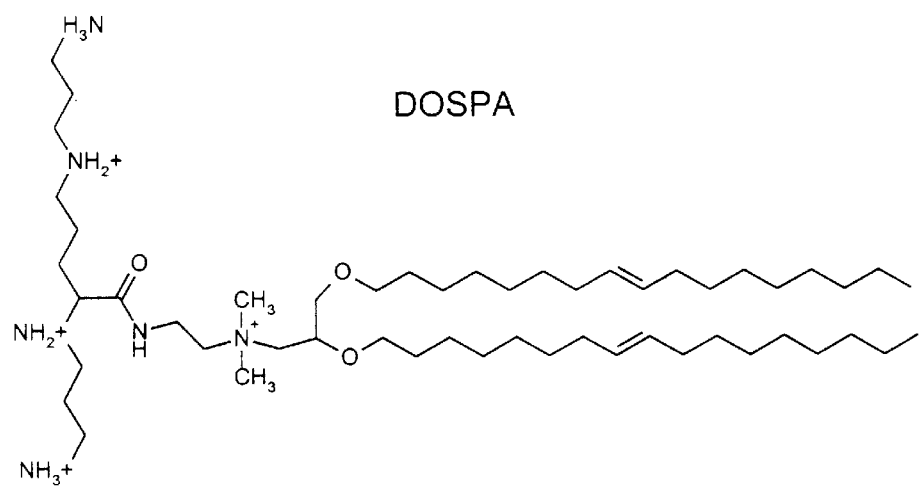
DOSPA
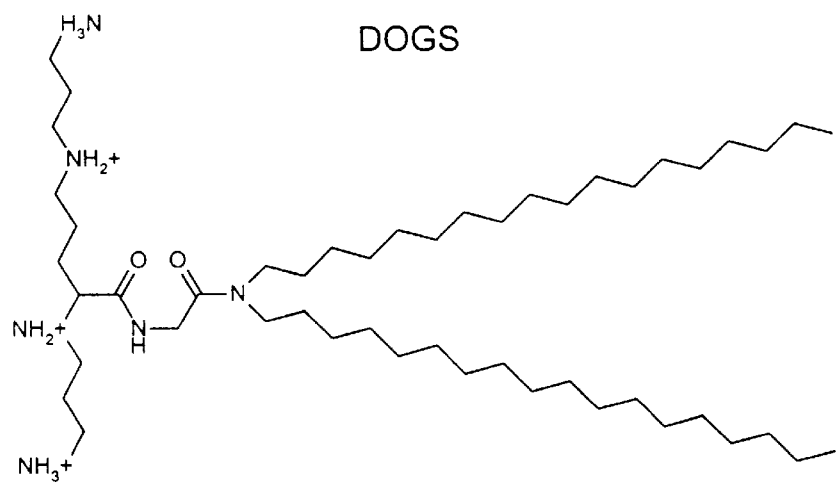
DOGS

*B1, B2 and B3, the three main components of the NFκB transcription factor. B1 is composed of the P50 homodimer, while B2 and B3 are composed of P65 and C-Rel proteins.

Figure 10
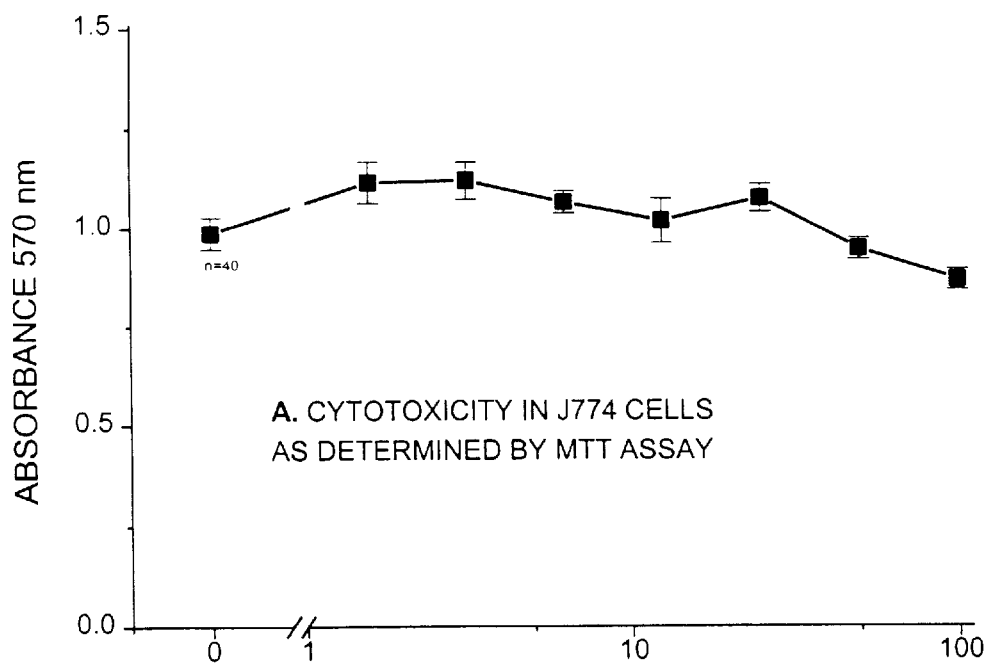
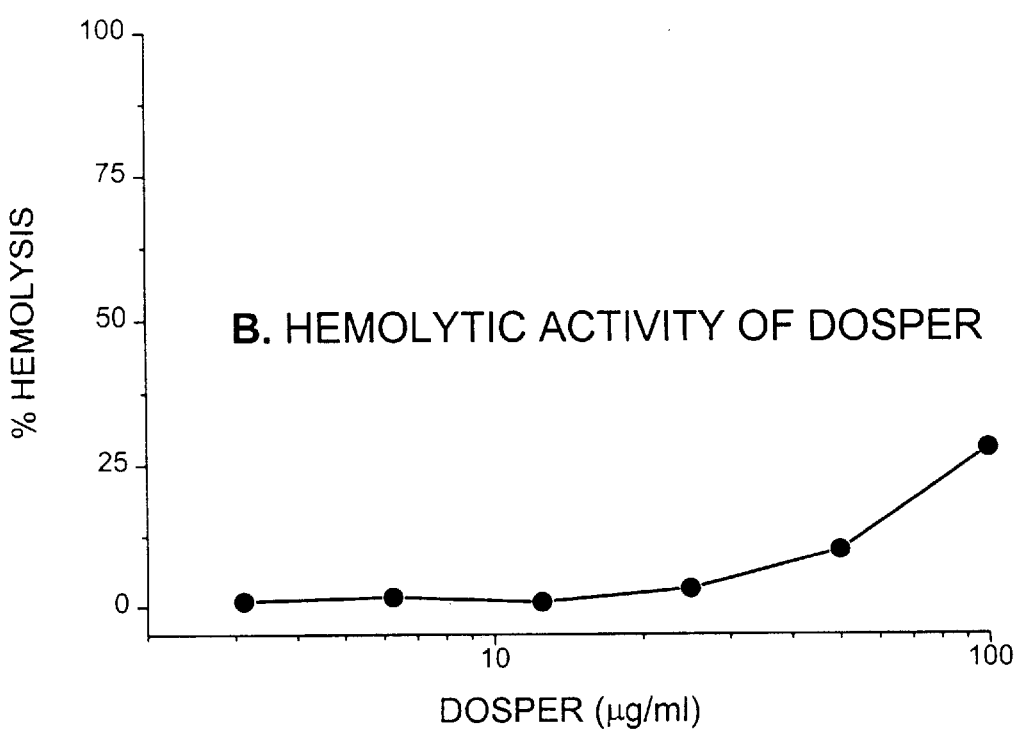

USE OF SYNTHETIC POLYCATIONIC AMPHIPHILIC SUBSTANCES WITH FATTY ACID OR HYDROCARBON SUBSTITUENTS AS ANTI-SEPSIS AGENTS

This application claims the benefit of U.S. Provisional Application No. 60/064,976, filed Nov. 10, 1997.

This discovery/invention was made in part with funds from the National Institutes of Health, Department of Health and Human Services under Grant No. PO1-CA59474 from the National Cancer Institute. Thus the United States Government retains certain rights in this discovery/invention.

BACKGROUND

Sepsis is a syndrome of systemic toxicity caused by the presence of bacteria and/or bacterial products in the blood stream.[1,2] This condition, often caused by bacteria which are part of the body's normal flora, occurs frequently when the body's defense mechanisms are compromised or overwhelmed, as in patients treated with immunosuppressants, corticosteroids, or radiotherapy, in infants with systemic meningococcal infections, post-surgical patients, patients with chronic liver disease, or with severe burns.[3] Increasingly, this condition is also precipitated in individuals treated with antibiotics for serious systemic infections. In these latter situations, antibiotics, while killing the bacteria, also cause the release into the bloodstream of a variety of products from the disintegrating bacteria.[4-7]

It is now well recognized by researchers and by clinicians that endotoxins, or lipopolysaccharides (LPS)—structural components of the outer membranes of Gram-negative bacteria[8,9]—play a pivotal role in the causation of the sepsis syndrome.[10,11] Lipopolysaccharides, released from bacteria, either by the body's natural defense systems, or by antibiotics, are recognized by a variety of cell types in the body, important among which is the monocyte/macrophage,[12] a subset of the white blood cells. When these cells sense the presence of lipopolysaccharide, they respond by producing numerous inflammatory mediators, including tumor necrosis factor-alpha (TNF-$\alpha$), interleukin-1 beta (IL-1$\beta$),[13-19] interleukin-6,[20-22] interleukin-8, interferon,[23] prostaglandins,[24-27] leukotrienes,[28,29] platelet activating factor,[30-32] and procoagulant tissue factor.[33,34] Other cells, such as the endothelium, produce nitric oxide.[18,35-39] The production of these mediators, under normal circumstances, is precisely regulated, and serves to orchestrate the body's defense mechanisms.

However, the unregulated overproduction of these substances[40] lead to the clinical syndrome termed "septic shock".[1,2] This syndrome is characterized by fever, hypotension, coagulopathy, hemodynamic derangement, tissue hypoperfusion, and multiple organ failure, which frequently culminates in death of the patient.[41-46] It is estimated that more than 300,000 cases of septic shock occur each year in the United States.[47]

The sepsis syndrome, however, is by no means an exclusive sequel of Gram-negative infections; about half of the mortality attributable to septic shock is associated with serious systemic Gram-positive organisms[47-49] which is clinically indistinguishable from that due to Gram-negative bacteria. Experimental data exist in the scientific literature which demonstrate that Gram-positive organisms can also induce a shock-like state in animal models[50-54] mimicking in most respects, shock induced by LPS. LPS-induced[55] as well as Gram-positive bacteria-induced systemic inflammatory responses[51] are preventable by anti-TNF-$\alpha$antibody. Gram-positive bacterial cell-walls,[50,56] and organism-free supernatants[57-59] obtained from Gram-positive bacterial cultures stimulate cytokine production from mononuclear cells. These observations, collectively, suggest that a final common pathway, involving proinflammatory cytokine overproduction,[60-62] may underlie the pathogenesis of septic shock, irrespective of the nature of the causative organism.

However, unlike Gram-negative sepsis, in which lipopolysaccharide is the primary molecule which initiates the systemic inflammatory responses, it is as yet unclear which component (or components) of the Gram-positive bacterium triggers the cytokine reponse[63] which ultimately overwhelms the normal homeostatic mechanisms of the body. Although increasing attention has focused on the cytokine-inducing properties of lipoteichoic acids (LTA),[64,65] structural components of the Gram-positive cell wall,[66] recent evidence, independently obtained from two different research groups, would appear to suggest that a minor high molecular weight glycolipid species which may or may not be chemically related to LTA[67-69] is the dominant cytokine-inducing molecule. The biological activity of this component, like LPS, is substantially enhanced in the presence of CD14, an LPS receptor, and is blocked by anti-CD14 antibody; furthermore, this component competitively inhibits LPS binding to cell surfaces.[68] It is reasonable, therefore, to hypothesize from these exploratory studies, that there may be present in Gram-positive bacteria, molecules of relatively low abundance which share some general physicochemical properties with that of LPS.

The therapy of septic shock remains, to date, primarily supportive, consisting of antibiotics to treat the underlying infection, as well as hemodynamic and respiratory support. Specific modalities of treating septic shock aimed at controlling those pathophysiological mechanisms that lead to the systemic inflammatory response which ultimately manifests in shock are, unfortunately, as yet unavailable[12,70,71] although clinical trials involving a variety of experimental approaches are currently in progress. With regard to the specific clinical problem of Gram-negative sepsis, one possible approach would be to target lipopolysaccharide itself by the use of an agent that would bind to and sequester this potent microbial product, thereby preventing its recognition by the monocyte/macrophage and other effector cells. This approach of "proximal intervention" would, in many respects, appear to be preferable to others directed at later events (e.g. therapeutic targeting of the inflammatory mediators), for once the monocyte/macrophage cell is activated, the cellular response is so diverse that a single pharmacological agent would be unlikely to modulate the effects of all the mediators produced. This approach of sequestering lipopolysaccharide, historically, has been addressed by the use of either polyclonal or monoclonal antibodies raised against the structurally conserved regions of lipopolysaccharide (so that the antibody would be cross-reactive against several lipopolysaccharide species from diverse Gram-negative bacteria).[72-81] However, clinical studies with polyclonal antibodies[82,83] have been difficult to interpret unequivocally[84] in spite of the fact that statistically significant levels of protection were reported by the authors. Numerous clinical trials[85-90] designed to test the therapeutic efficacy of monoclonal antibodies have failed to establish that the use of such antibodies are of clinical value. One possible reason could be that the region on the lipopolysaccharide molecule recognized by the antibodies is "cryptic" or hidden, at the molecular level, by other regions of the toxin molecule.

Several LPS-binding proteins of non-immunologic origin which are known to bind and neutralize the effects of endotoxin are currently being evaluated as candidate therapeutic agents. An endotoxin-binding protein[91,92] obtained from the Horseshoe crab *Limulus polyphemus* (U.S. Pat. Nos. 5,627,266; 5,614,369) and a protein found in neutrophil granules, called Bactericidal/Permeability-increasing Protein (BPI) 93–103 (U.S. Pat. Nos. 5,652,332; 5,646,114; 5,643,570; 5,639,727; 5,523,2885,494,896; 5,447,913; 5,420,019; 5,348,942; 5,348,942) have been patented for potential application in the treatment of septic shock. These proteins bind to lipopolysaccharide and neutralize its toxicity. Yet more recently, another protein belonging to a family of phospholipid-binding proteins called Annexins[104–108] has been patented (U.S. Pat. No. 5,658,877). This protein, presumably, also binds to LPS and inhibits its toxicity. Unfortunately, the production of these proteins for widespread use as therapeutic agents is likely to prove costly and will potentially impact significantly upon health care costs in treating this disease.

The toxic center of the lipopolysaccharide molecule is a glycolipid called lipid A, whose structure is shown diagrammatically in FIG. 1. Chemically, lipid A consists of a β-(1,6)-linked bis-glucosamine backbone with amide-and ester-linked fatty acids, and two phosphate groups on the backbone at the 1 and 4' positions.[9,109–112] The structure of lipid A is highly conserved and therefore very similar among Gram-negative bacteria. Because it is the toxic center of the endotoxin molecule, it therefore presents a logical molecular target for compounds designed to bind lipopolysaccharide.

The anionic and amphiphilic nature of lipid A[109,110,112] enables it to bind to numerous substances which are positively charged and also possess amphipathic character. However, the binding of such molecules to lipopolysaccharide alone does not neutralize LPS toxicity, which requires that certain molecular characteristics be mandatorily present if adequate neutralization of endotoxicity is to occur. We have, over the last several years, characterized the interactions of lipopolysaccharide with a number of classes of molecules including proteins,[113,114] peptides,[119–122] pharmaceutical compounds,[123,124] and other synthetic polycationic amphiphiles.[125,126] We discovered, during these studies, that molecules with multiple protonatable positive charges which are so disposed that the distance between the charges are approximately equal to the theoretical distance between the two negative charges present on the two phosphate groups of the lipid A molecule enable the binding of such molecules to lipid A, and also to lipopolysaccharide, the parent molecule.[123,124] We have further determined that the presence of appropriately positioned hydrophobic groups enhances and stabilizes the binding of such molecules.[124,125]

As discussed above, there is a sufficient body of knowledge in the scientific literature to render tenable the hypothesis that, because molecules that resemble LPS, or of its lipid A moiety, in gross physicochemical terms may exist in the Gram-positive organism, some cationic amphiphiles may also sequester these as yet uncharacterized cytokine-inducing molecules and inhibit the effects of Gram-positive organisms.

The present discovery reported in this document describes our studies designed firstly to demonstrate the use of such cationic amphiphilic molecules in binding lipopolysaccharide, and in inhibiting its toxicity in vitro and in vivo; secondly we show that such cationic amphiphilic molecules also inhibit the deleterious effects caused by Gram-positive organisms in an animal model. We do not as yet understand the basis or the mechanism by which such cationic amphiphilic molecules afford protection against Gram-positive bacteria, and we presume that it is a consequence of the binding and subsequent neutralization of one or more species of molecule(s) present in Gram-positive organism which bear some similarities to LPS, or of its lipid A moiety, in terms of general physicochemical properties. Representative examples of the cationic amphiphilic molecules employed in these studies (shown in FIG. 2) include 1,3-di-oleoyloxy-2-(6-carboxyspermyl)-propylamide (available commercially as "DOSPER" from Boehringer-Mannheim Corporation, Indianapolis, Ind.), 2,3-dioleoyloxy-N[2(sperminecarboxamido)ethyl]-N,N-dimethyl-1-propanaminium trifluoroacetate ("DOSPA"; available as LipofectAMINE™ from Life Technologies, Gaithersburg, Md.), dioctadecylamidoglycylspermine ("DOGS"; available as Transfectam™ from Promega Corporation, Madison, Wis.).

These compounds were originally developed[127–133] and are currently being marketed as agents that will facilitate the transfection (transport) of DNA into recipient cells. A list of U.S. patents related to the development and use of these molecules, that have been filed to date is provided in Table 1.

TABLE 1

Partial list of U.S. Patents relating to the development and applications of lipopolyamine compounds

| CATEGORY | U.S. Pat. No. | INVENTORS | TITLE |
| --- | --- | --- | --- |
| Lipofect- | 5,627,159 | Shih P J et al | Enhancement of lipid cationic transfections . . . |
| AMINE ™ | 5,578,475 | Jessee J A | Composition and methods for transfecting . . . |
| Transfectam ™ | 5,650,096 | Harris D J et al | Cationic amphiphiles for intracellular delivery . . . |
| | 5,635,487 | Wolff J A et al | Amphipathic, micellar delivery systems . . . |
| | 5,616,745 | Behr J P et al | Lipopolyamines, their preparation and their use |
| | 5,476,962 | Behr J P et al | New lipopolyamines, their preparation and their use |
| | 5,171,678 | Behr J P et al | Lipopolyamines, their preparation and use |
| DOSPER | 5,661,018 | Ashley G W et al | Cationic phospholipids for transfection |
| | 5,651,981 | Ashley, G W et al | Cationic phospholipids for transfection |
| | 5,650,096 | Harris D J et al | Cationic amphiphiles for intracellular delivery . . . |
| | 5,283,185 | Epand R M et al | Method for delivering nucleic acids into cells |
| OTHER | 5,521,291 | Curiel D T et al | Conjugates for introducing nucleic acid . . . |
| | 5,614,503 | Chaudhary N et al | Amphipathic nucleic acid transporter |
| | 5,635,380 | Naftilan A J et al | Enhancement of nucleic acid transfer . . . |
| | 5,342,945 | Bergeron R J et al | Anti-neoplastic, anti-viral, or . . . |
| | 5,527,928 | Nantz M H et al | Cationic transport reagents |

TABLE 1-continued

Partial list of U.S. Patents relating to the development and applications of lipopolyamine compounds

| CATEGORY | U.S. Pat. No. | INVENTORS | TITLE |
|---|---|---|---|
| | 5,459,127 | Felgner, P L et al | Cationic lipids for intracellular delivery . . . |
| | 5,264,618 | Felgner P L et al | Cationic lipids for intracellular delivery . . . |

Nonetheless, there remains a need in the art for a demonstration of the use of such molecules in binding lipopolysaccharide and in inhibiting its toxicity.

SUMMARY OF INVENTION

In response to this need, we describe the ability of synthetic cationic amphiphilic molecules to bind and sequester bacterial lipopolysaccharide and inhibit its toxicity in vitro and in vivo; furthermore, we show also that such molecules inhibit the deleterious effects of the administration of Gram-positive organisms, presumably by sequestration and subsequent neutralization of one or more species of molecules present in Gram-positive organisms that bear some physicochemical similarities to LPS, or of its lipid A moiety. Such cationic amphiphilic molecules would have a molecular structure comprised of linear or branched backbone derived from polymethylenes or alkylamines and bear at the termini two or more protonatable positively charged groups derived from primary-amino, imidazolinium, or N, N'-unsubstituted amidinium, or guanidium functions. They would also possess one or more lipophilic groups derived from fatty acids or hydrocarbon substituents, attached to the backbone via amide, ester, carbamate, or urethane linkages. In addition to binding and sequestering LPS or other microbial products present in Gram-positive bacteria that share structural and/or physical-chemical properties with those of LPS, or of its lipid A moiety, these molecules prevent recognition of LPS and/or other cytokine-inducing molecules by monocytes/macrophages, inhibit the induction of cytokine gene transcriptional activation by LPS, and inhibit LPS-induced production of cytokines and nitric oxide; furthermore, such compounds inhibit lethality in mice caused by the administration of Gram-positive organisms. Therefore, such cationic amphiphilic molecules may find use as low cost, yet effective and broad-spectrum therapeutic agents for the treatment of sepsis and septic shock. Such agents may enhance the treatment of Gram-positive and/or Gram-negative sepsis or septic shock associated with septicemia. In addition, in view of the current reliance on systemic antibiotic therapy, the agents of the invention may enhance the effect of such antibiotics by reducing or preventing pathological sequelae known to those in this field that are due to dysregulated production of one or more inflammatory mediators arising from antibiotic-induced release of endotoxins from Gram-negative bacteria, or arising from antibiotic-induced release of lipopolysaccharide-like compounds present in Gram-positive bacteria.

DESCRIPTION OF THE DRAWINGS

FIG. 2. Chemical structures of representative cationic amphiphiles

FIG. 10. DOSPER is nontoxic to cells and is non-hemolytic.

Table 1: Partial list of U.S. Patents relating to the development and applications of lipopolyamine compounds.

Table 2: DOSPER decreases endotoxin-mediated lethality in a D-galactosamine-sensitized model of endotoxin shock in CF-1 mice.

Table 3: Comparison of the protective effects of DOSPER and Transfectam administered at different time-points against LPS in D-galactosamine-sensitized mice.

Table 4: Protective effect of DOSPER in D-galactosamine-sensitized mice challenged with *E. coli* and cell wall-active antibiotics.

Table 5: DOSPER Protects D-galactosamine-sensitized mice challenged with *Staphylococcus aureus*.

EXAMPLES

Example 1

Figure 1:
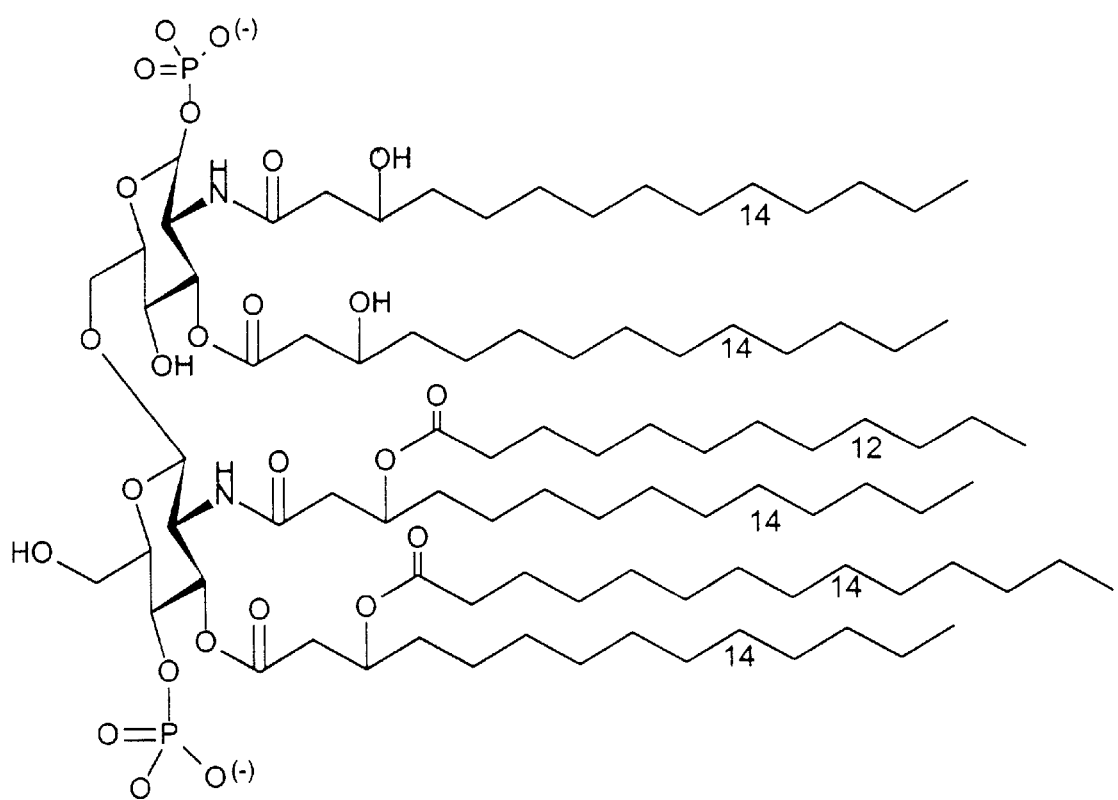
FIG. 1. Chemical structure of lipid A, the endotoxically active center of bacterial lipopolysaccharide.
Figure 3:
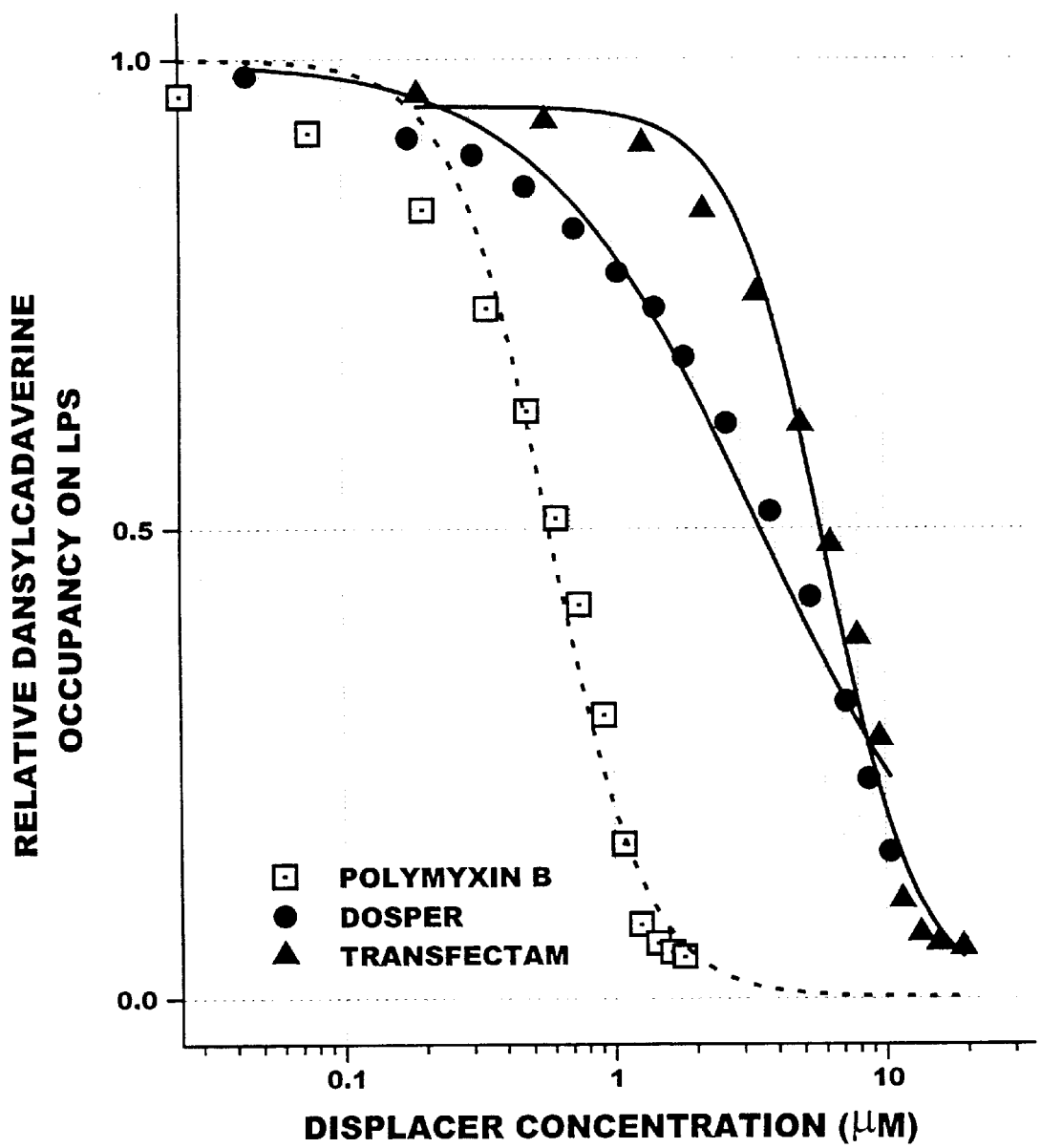
FIG. 3. Binding of Transfectam™ and DOSPER to purified lipopolysaccharide (LPS) assayed by dansylcadaverine (fluorescent probe) displacement.

Our initial studies were designed to establish that the molecules described above will bind with high affinity to bacterial lipopolysaccharides. We have evaluated Transfectam™ and DOSPER as prototype compounds representative of the lipopolyamine class. Analytical mass spectrometric analysis performed on these two products (as supplied by the vendors) established and confirmed the chemical identity of these substances. The data shown in FIG. 3 establish that Transfectam™ and DOSPER bind to purified lipopolysaccharide from *E. Coli* K12-D31m4 (obtained from List Biologicals, Campbell, Calif.) as determined by the highly sensitive dansylcadaverine fluorescent probe displacement method.[120] In this assay, the binding of the fluorescently tagged molecule to the lipid A region of LPS results in a characteristic blue-shift and intensity enhancement in the emission spectrum of dansylcadaverine.

Compounds which bind LPS displace, in a competitive manner, the bound dansylcadaverine probe, resulting in a progressive, concentration-dependent quenching of fluorescence. Probe displacement has been analyzed as a function of competitive binding of displacer molecule concentration.

Comparisons of dansylcadaverine displacement curves to evaluate relative potencies of the compounds were performed by simultaneous curve-fitting with a four-parameter logistic equation to obtain accurate $ED_{50}$ values (displacer concentration corresponding to 50% probe displacement)[120] The $ED_{50}$ values for Transfectam™ and DOSPER are, respectively, 6.1 and 3.5 µM. Polymyxin B, a peptide antibiotic, known to bind to the lipid A region[134] of lipopolysaccharide and inhibits its toxicity[135] was used as a control for these studies. The $ED_{50}$ for polymyxin B was determined to be 0.58 µM. Thus, the affinity of interaction of Transfectam™ and DOSPER with lipopolysaccharide are about an order of magnitude lower than that of polymyxin B, but nevertheless, still of relatively high LPS binding affinity. Although DOSPER and Transfectam™ possess primary amino groups on the termini of their backbones, based on our earlier work on a variety of cationic amphiphiles,[113-114,119-126] we predict that molecules similar to DOSPER and Transfectam™, but possessing isofunctional groups such as imidazolinium, or N, N'-unsubstituted amidinium or guanidinium groups would also be effective.

Example 2

Figure 4:
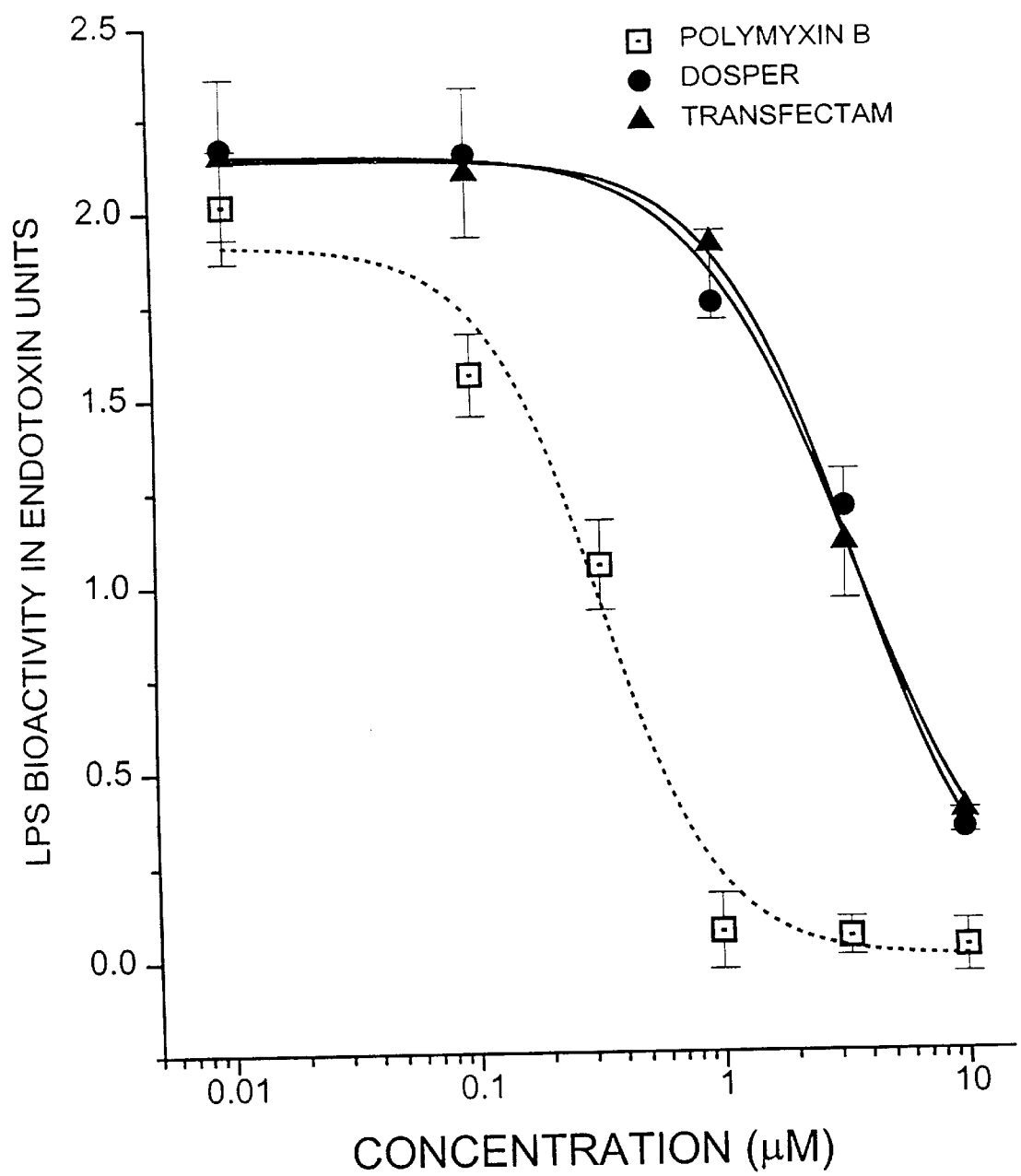
FIG. 4. Transfectam™ and DOSPER inhibit activation of the endotoxin-sensitive Limulus amebocyte lysate (LAL) clotting cascade by LPS.

Having established that these molecules bind to LPS, it was necessary to ascertain whether such binding would result in the inhibition of the biological activity of the endotoxin molecule. The data shown in FIG. 4 prove that Transfectam™ and DOSPER inhibit lipolysaccharide-induced activation of the *Limulus polyphemus* coagulation cascade.

This assay is the accepted standard test used by the U.S. FDA to determine the presence of biologically-active endotoxin in parenteral solutions. A chromogenic version of the assay[136,137] purchased from BioWhitaker (Walkersville, Md.), was used in these tests. A constant concentration of LPS (4 endotoxin units) was incubated with varying doses of the compounds (or polymyxin B, as control) at 37° C. for 10 min. The mixture was then assayed for the presence of free, biologically-active LPS. Both Transfectam™ and DOSPER decrease the amount of bioactive LPS in a dose-dependent manner, showing that these compounds effectively sequester LPS, and the resultant complexes lose their ability to activate the coagulation cascade. Polymyxin B was determined to be about 10 times more potent than either Transfectam™ or DOSPER in inhibiting LPS activity in this assay, consistent with the binding profiles shown in FIG. 3. These data show that compounds such as Transfectam™ and DOSPER can effectively neutralize the toxic activity of LPS.

Example 3

As mentioned earlier, endotoxin manifests most of its toxic activities in septic shock by stimulating host cells such as monocytes/macrophages to release proinflammatory mediators. It was therefore important to establish that the cationic amphiphilic molecules employed in these studies would, in fact, be capable of inhibiting the production of these mediators in monocytes stimulated with endotoxic lipopolysaccharide. The data presented in FIG. 5 establish that both Transfectam™ and DOSPER will inhibit the LPS-induced production of nitric oxide, tumor necrosis factor-α and interleukin-6 from a mouse-derived macrophage-like cell line, J774.A 1 (procured from the American Tissue Type Culture Collection, Washington D.C.).

Figure 5:
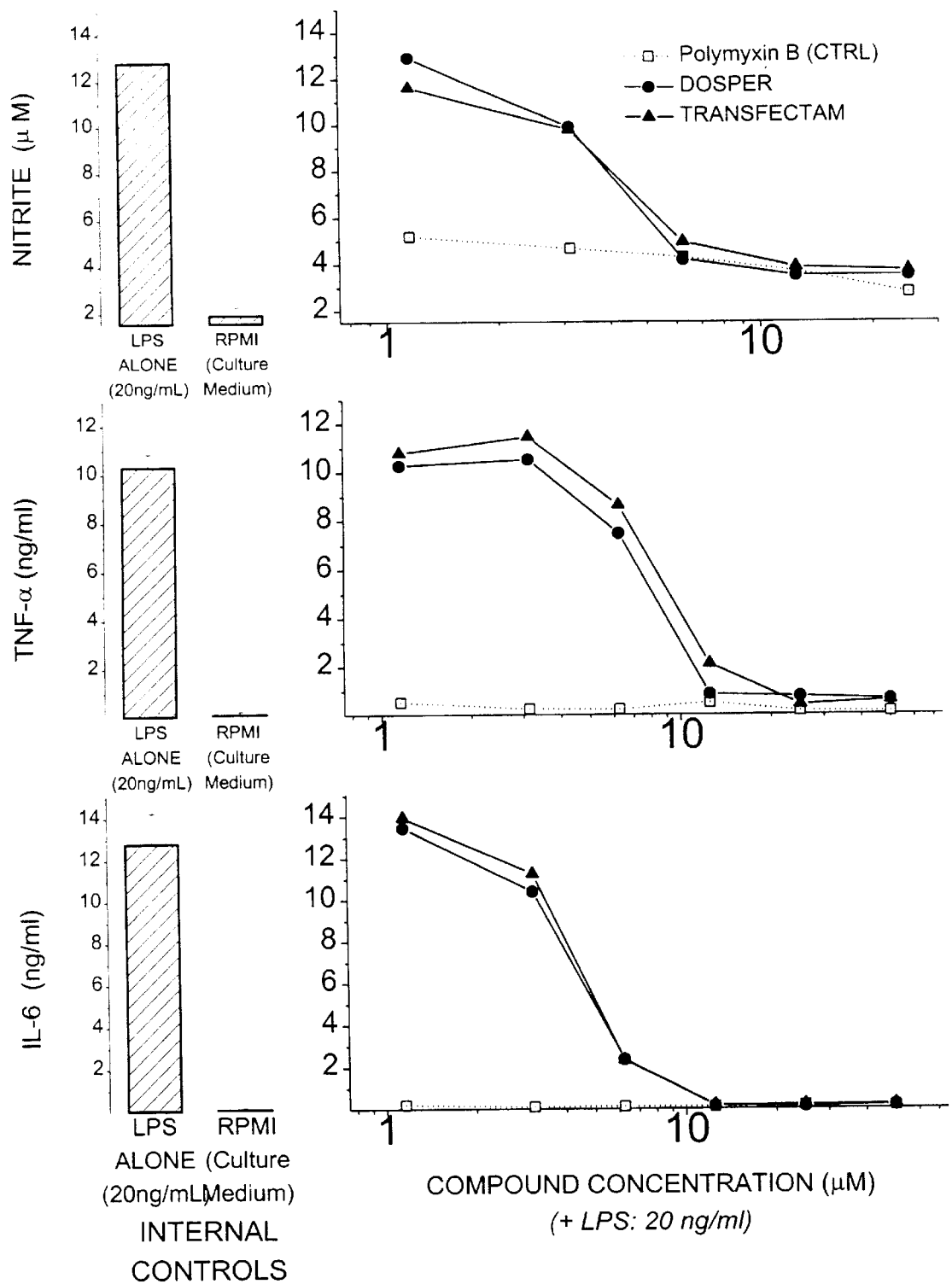
FIG. 5. Transfectam™ and DOSPER inhibit LPS-induced production of nitric oxide (measured as nitrite), tumor necrosis factor-α(TNF-α) and interleukin-6 (IL-6) by a macrophage-like cell-line, J774.A1.

J774.A1 cells were plated in polystyrene 96-well tissue culture microtiter plates at a density of $1.5 \cdot 10^6$ cells/ml. They were then stimulated with either LPS alone (20 ng/ml), or LPS (20 ng/ml) preincubated with varying concentrations of Transfectam™, DOSPER or polymyxin B. As a negative control, only tissue culture medium (RPMI-1640; Sigma Chemicals, St. Louis, Mo.) was added. Supernatants were harvested at 12 h following stimulation. Nitric oxide production was measured as total nitrite by the Griess reaction.[138] TNF-α and IL-6 were quantitated using specific enzyme-linked immunosorbent assay (ELISA) systems (Genzyme, Cambridge, Mass.). The results presented in FIG. 5 show that both DOSPER and Transfectam™ inhibit LPS-induced production of nitric oxide, TNF-α and IL-6 in a dose-dependent fashion. Polymyxin B, once again, is about an order of magnitude more potent than either compound. Inhibition of inflammatory mediator production by white cells in response to endotoxic LPS stimulation is an essential requisite of endotoxin binding molecules suitable for therapeutic use in treating Gram-negative sepsis.

Example 4

Figure 6:
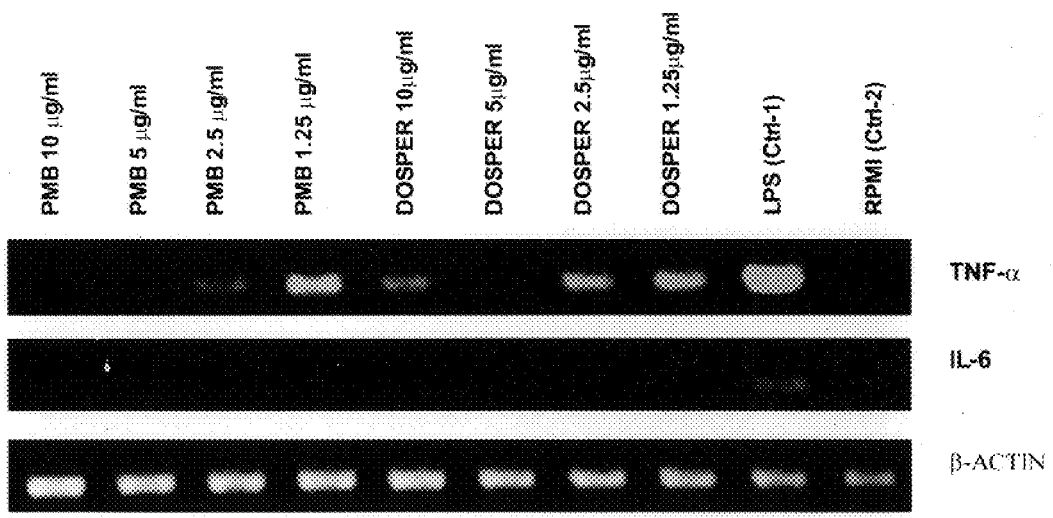
FIG. 6. DOSPER inhibits TNF-α and IL-6 mRNA steady-state levels in J774.A1 cells stimulated with LPS.

It is important to understand the mechanisms by which inhibition of the biological activity of LPS by DOSPER and related compounds is achieved. We have postulated that the high affinity binding of such molecules to LPS prevents the latter from binding to receptor molecules on macrophages and activating them. Since one of the early events in the molecular activation pathway of macrophages by LPS, preceding the synthesis and subsequent secretion of proinflammatory mediators such as TNF-α and IL-6 is the initiation of new gene transcription, we have assessed the ability of DOSPER to inhibit the induction of gene transcription by LPS. The data shown in FIG. 6 provides evidence that DOSPER inhibits transcriptional activation[139,140] by LPS.

J774.A1 cells ($3 \times 10^6$ cells) were stimulated for 60 min with either LPS alone (20 ng/ml) or LPS preincubated with varying concentrations of DOSPER (or polymyxin B). RPMI-1640 alone was added in equal volume to cells to serve as an internal negative control. Total RNA was extracted using conventional phenol-chloroform extraction procedures. TNF-α, IL-6 (and β-actin, a constitutively expressed house-keeping gene, used as an internal control) mRNA was quantified using reverse transcriptase/polymerase chain reaction (RT-PCR) procedures. DOSPER completely inhibits IL-6 mRNA levels at all concentrations tested (middle panel) while its effect on TNF-α is less pronounced, but nevertheless significant. Inhibition of TNF-α mRNA by polymyxin B is clearly evident at higher concentrations.

Example 5

Prior to gene expression itself, certain intracellular signaling events occur that transduce the signal from the cell surface receptor molecules to the nucleus where the DNA sequences of appropriate proteins that must be synthesized in response to the signal are transcribed into messenger RNA (mRNA). Preeminent among such intracellular mediators in LPS-responsive cells, such as the macrophage, is a protein termed Nuclear Factor Kappa B (NFκB).[139,141-145] When macrophages are stimulated with LPS, NFκB is translocated from the cytosol where it is normally present in an inactive form, to the nucleus, where it binds to promoter regions on LPS-specific genes, initiating their transcription. Therefore, the translocation of NFκB is a very early event, occurring within 15 min of exposure to LPS. In order to further confirm our hypothesis that LPS-sequestering agents such as DOSPER inhibit the very first step of cellular activation, namely, the recognition of LPS by cell surface receptors, we have analyzed the nuclear translocation of NFκB in J774.A1 cells treated with LPS premixed with DOSPER or polymyxin B. Nuclear proteins extracted from stimulated cells were incubated with radioactively ($^{32}P$) labeled double-stranded oligonucleotide whose sequence corresponds to the NFκB binding sites on genes that are specifically activated by NFκB. The nuclear protein-oligonucleotide mixtures were then analyzed by electrophoretic mobility shift assay (EMSA). Transcription factors such as NFκB, when bound to oligonucleotide, retard the mobility of the latter in the EMSA assay.

Figure 7:
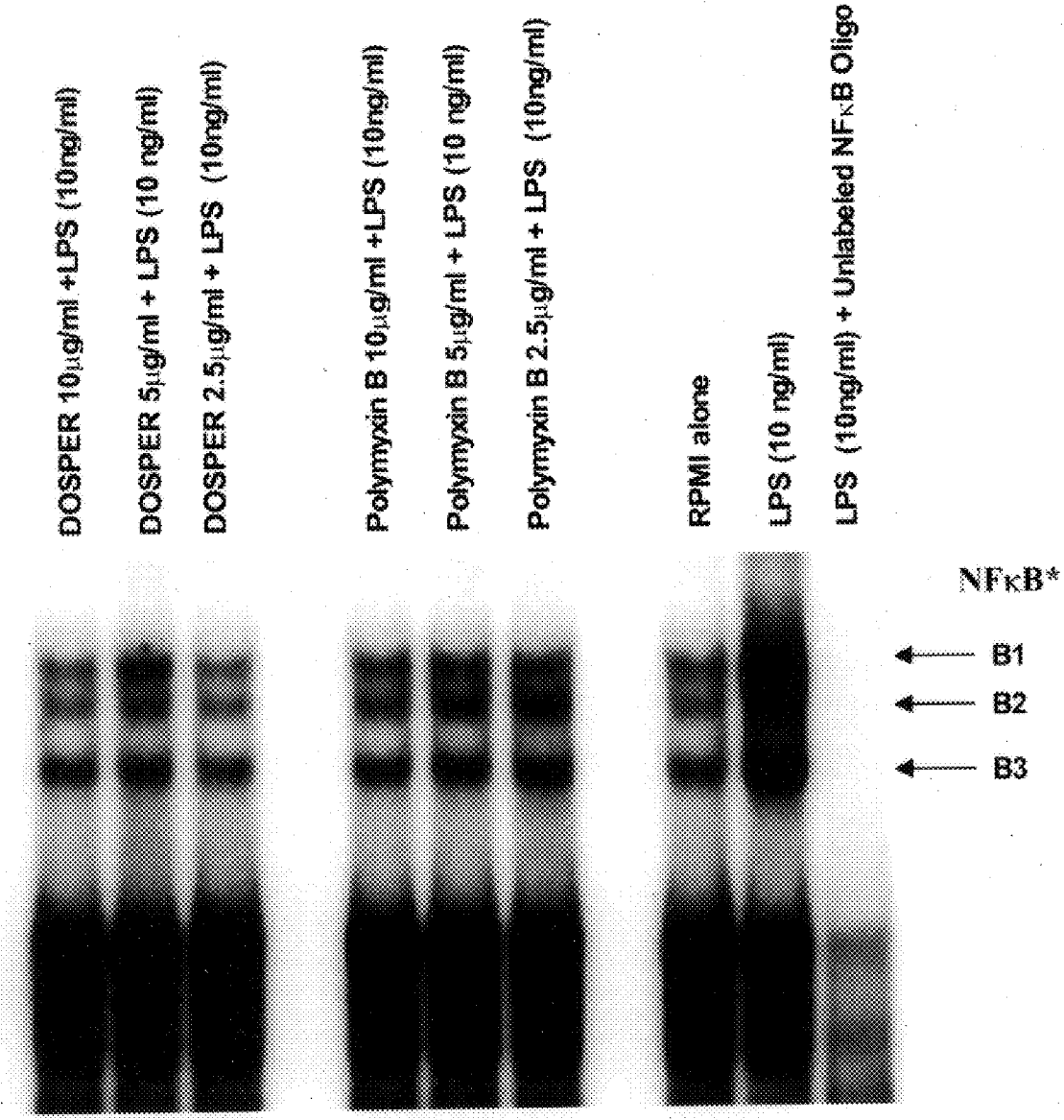
FIG. 7. DOSPER inhibits Nuclear Factor Kappa B (NFκB) translocation in J774.A1 cells stimulated with LPS.

The actual identity of the transcription factor is identified by its apparent molecular weight and by the ability of large excesses of unlabeled oligonucleotide to competitively inhibit the radioactively labeled probe. The results of such experiments are shown in FIG. 7 and demonstrate that DOSPER inhibits the translocation of NFκB as potently as polymyxin B. In contrast, cells treated with LPS alone show significantly higher NFκB activity in the nuclei of activated cells. These results clearly show that early events following the recognition of LPS by cells are inhibited by lipopolyamine compounds such as DOSPER, which strengthen the premise that complexation of such compounds with LPS render the toxin inactive in terms of its ability to stimulate macrophages and other cells to produce inflammatory mediators.

Example 6

Since these cationic amphiphilic molecules inhibit LPS-mediator production, we predicted that they would be of value in the treatment of Gram-negative sepsis and septic shock. To test this prediction, we have used a well-established animal model of experimental sepsis in which the toxic properties of LPS can be measured quantitatively. Table 2 summarizes the protective effects of DOSPER against LPS in D-galactosamine-sensitized mice. Adult female CF-1 mice (Jackson Laboratories, Bar harbor, Mich.) weighing 28–32 g were sensitized to the lethal effects of endotoxin by administration of D-galactosamine (18 mg/mouse intraperitoneally [i.p.].) using a standard protocol that has previously been described by us[146–148] and others.[149–151] The animals were then challenged intraperitoneally with different doses of purified *E. coli* LPS, either alone, or preincubated with DOSPER, at varying concentrations. DOSPER alone served as control. The $LD_{80}$ dose for LPS (that is, the dose of LPS required to achieve 80% lethality due to endotoxin-induced septic shock) in this animal model is typically between 10 and 20 ng/mouse. DOSPER, when used at sufficiently high doses completely prevents mortality in mice receiving 50 ng LPS, a dose of endotoxin that should prove lethal in 100% of the animals.

TABLE 2

Protective effect of DOSPER in D-galactosamine-sensitized mice challenged with *S. abortus equi* LPS

| LPS CHALLENGE | DOSPER DOSE (µg/mouse) | | |
|---|---|---|---|
| (ng/mouse) | 0 | 10 | 40 |
| 0 | — | 0/5 | 0/5 |
| 10 | 9/10 | 1/10* | 0/5* |
| 20 | 5/5 | 2/5 | 0/5* |
| 50 | — | — | 0/5 |

Example 7

In more detailed studies, the results of which are summarized in Table 3, we have sought to examine the protection afforded by DOSPER or Transfectam™ when administered at different time-points with respect to LPS challenge. When LPS and DOSPER or Transfectam™ are administered intraperitoneally at the same time (injected separately, and not as premixed solutions as were done in experiments shown in Table 2), virtually complete protection against LPS lethality is observed, demonstrating that the lipopolyamines will bind LPS and neutralize its toxicity in vivo. This protective effect is observed when DOSPER is injected 15 min prior to LPS challenge, albeit of lower magnitude. Early administration (1 h prior to LPS) of the compound, however, is not effective. This is probably due to the rapid clearance of the lipopolyamines from the systemic circulation. Importantly, significant protection (about 50%) is achieved when DOSPER is administered up to 4 h following LPS challenge. This suggests that compounds such as DOSPER may have potentially significant therapeutic value in treating patients with established septic shock.

TABLE 3

Effect of time of lipopolyamine administration on LPS-induced lethality in D-galactosamine-sensitized mice

| GROUP* | TIME OF LIPOPOLYAMINE† ADMINISTRATION | LETHALITY‡ |
|---|---|---|
| DOSPER | | |
| 1. | Control | 11/12 |
| 2. | 0 h | 1/12** |
| 3. | −1 h | 10/12 |
| 4. | −15 min | 3/12** |
| 5. | +1 h | 7/11 |
| 6. | +2 h | 7/12 |
| 7. | +4 h | 7/12 |
| TRANSFECTAM | | |
| 1. | Control | 10/10 |
| 2. | 0 h | 0/10** |
| 3. | −1 h | 6/10 |
| 4. | +1 h | 5/10 |
| 5. | +2 h | 9/10 |
| 6. | +4 h | 9/10 |

Table 3:
*Each D-galactosamine-sensitized mouse received 20 ng *S. abortus equi* LPS.
†Transfectam or DOSPER dose: 40 µg/mouse. Control animals received 0.2 ml of saline instead of lipopolyamine. 0 h: animals were injected with lipopolyamine i.p. immediately after LPS/D-galactosamine challenge.
‡Numbers denote dead/total.
**$p < 0.005$ Example 8

Figure 8:
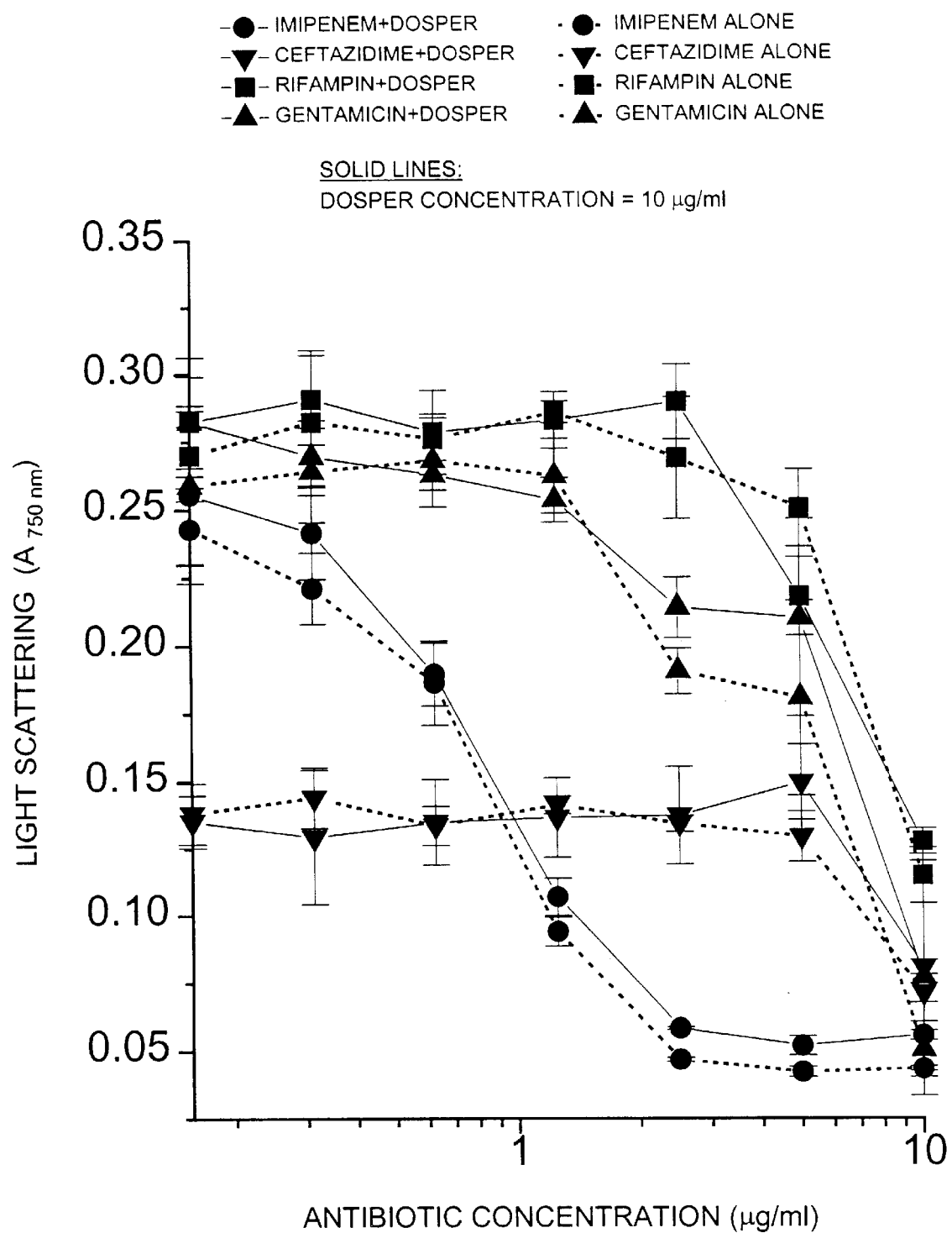
FIG. 8. DOSPER does not enhance the microbicidal activity of antibiotics.

In order to evaluate if DOSPER will also afford protection in animal models of Gram-negative septic shock which more closely mimic the clinical situation than the experiments described under Example 7, we evaluated the compound in a variant of the D-galactosamine mouse lethality model wherein LPS is released in vivo by the action of antibiotics on live *E. coli* O111:B4.[4,152] In these experiments, mice received graded doses of a suspension in phosphate-buffered saline of mid log phase harvested *E. coli*, and, by separate i.p. injection, 0.2 ml of either imipenem-cilastin (Merck Inc., Rahway, N.J.) or ceftazidime (Glaxo-Wellcome, Research Triangle Park, N.C.) at concentrations of 2.5 mg/ml and 5 mg/ml, respectively. DOSPER (40 µg/mouse; 0.2 ml volume) or saline (0.2 ml) was also injected i.p. at the same time. Lethality was determined at 24 h. Statistical significance of lethality data were analyzed by the Fisher exact probability test. Ceftazidime has been shown to cause more LPS release, both in vitro,[4] and in vivo,152 than imipenem and, therefore, provides less protection than imipenem in the D-galactosamine model.[152] We reasoned that if DOSPER were to function as a scavenger of circulating LPS, it would enhance, to a greater degree, the protection obtained with ceftazidime than with imipenem. As expected, DOSPER when coadministered with ceftazidime causes a distinct shift to the right in the lethality profiles (Table 4), signifying an increase in the $LD_{50}$ of more than an order of magnitude of *E. coli* challenge dose which is not apparent in imipenem-treated mice. Of interest, DOSPER appears also to afford some protection in non-antibiotic-treated mice (4/10 in DOSPER-treated mice versus 6/6 when challenged with $10^4$ organisms). DOSPER has no detectable intrinsic antimicrobial effects on *E. coli* up to concentrations of 75 μg/ml. Since polycationic molecules have been known to permeabilize the Gram-negative bacterial outer membrane,[153,154] we also ruled out possible potentiation effects of DOSPER on the microbicidal activity of several classes of antibiotics (FIG. 8). This effect is therefore probably attributable to the elimination by the compound of LPS released spontaneously by the action of plasma components such as complement.[155]

TABLE 4

Protective effect of DOSPER in D-galactosamine-sensitized mice challenged with *E. coli* and cell wall-active antibiotics

| E. coli Challenge (CFU/mouse) | Saline | Saline + DOSPER | Imipen. + Saline | Imipen. + DOSPER | Ceftaz. + Saline | Ceftaz. + DOSPER |
|---|---|---|---|---|---|---|
| $10^2$ | 0/6 | — | — | — | — | — |
| $10^3$ | 4/6 | 3/5 | 0/4 | — | 0/4 | — |
| $10^4$ | 6/6 | 4/10* | 0/10 | — | 1/10 | — |
| $10^5$ | — | 9/10 | 6/10 | 2/9 | 8/10 | 2/10* |
| $10^6$ | — | 10/10 | 6/10 | 7/10 | 10/10 | 6/10* |
| $10^7$ | — | 5/5 | — | 9/10 | — | 7/10 |

DOSPER (40 g/mouse) and imipenem (0.5 mg/mouse) or ceftazidime (1.0 mg/mouse) were administered at the same time as *E. coli* challenge. Collated results of two experiments. Ratios denote dead/total.
*P < 0.005.

Example 9

Figure 9:
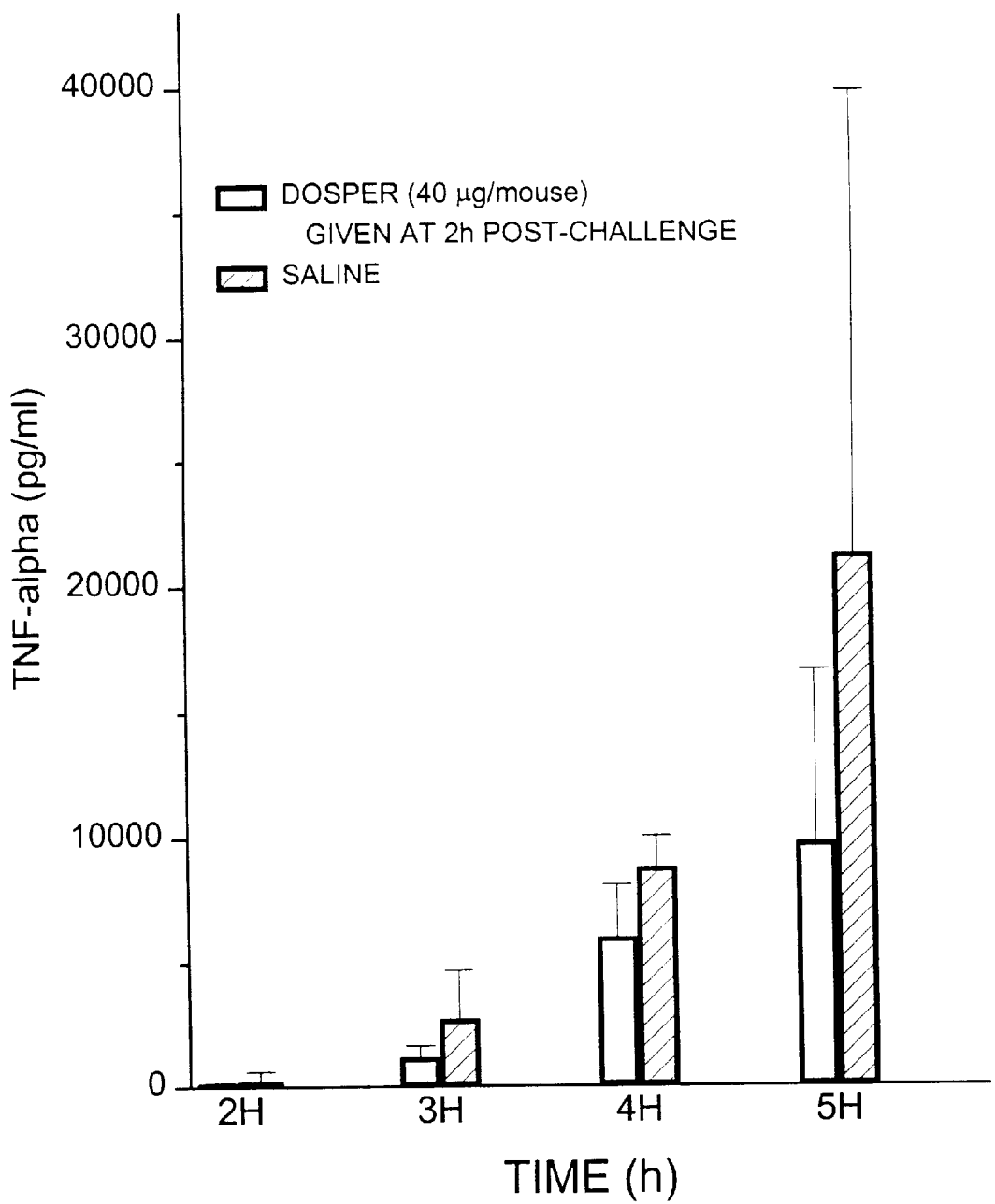
FIG. 9. DOSPER inhibits in vivo TNF-α levels in *S. aureus*-challenged mice

As described under Background, we hypothesize that certain species of molecules, resembling LPS in gross physicochemical terms, may exist in the Gram-positive organism, and which contribute to the cytokine-inducing properties of such organisms. We further hypothesize that, because such molecules may resemble LPS, or its lipid A moiety in that such molecules, like LPS and lipid A, may also be anionic amphiphiles, certain cationic amphiphilic molecules may bind and neutralize their activity. We have tested this hypothesis by ascertaining if DOSPER would protect D-galactosamine-sensitized mice challenged with *Staphylococcus aureus*, a Gram-positive organism. As shown in Table 5, DOSPER completely prevents lethality induced by *S. aureus*. Preliminary evidence has also been obtained which show that protection by DOSPER is paralleled by decreased serum TNF-α levels (FIG. 9). We have verified that DOSPER, as with *E. coli*, has neither any significant antimicrobial activity up to 40 μg/ml, the dose used in the animal experiments, nor does it enhance the antibacterial effect of imipenem.

TABLE 5

DOSPER Protects D-galactosamine-sensitized mice challenged with *Staphylococcus aureus*

| S. aureus Challenge CFU/mouse | Imipenem + Saline | Imipenem + DOSPER |
|---|---|---|
| $10^6$ | 0 | 0 |
| $10^7$ | 7/20 | 0/20 |
| $10^8$ | 15/20 | 0/20 |

Example 10

DOSPER is neither toxic to J774.A1 cells employed in our in vitro experiments, nor does it cause significant hemolysis of human erythrocytes even up to 100 μg/ml (FIG. 10), which is a common, yet undesirable consequence of the membrane-disruptive behavior of many surface-active cationic amphiphiles. In other experiments, mice receiving cumulative does of 120 μg of DOSPER tolerated the compound well, showing no detectable signs of acute toxicity. This desirable attribute of low toxicity appears to be a common property of several similar compounds now being used as DNA transfection agents.

DOSPER is devoid of adverse effects on CHO-K1 cells in vitro up to a concentration of 30 μg/ml (Product Literature on DOSPER, supplied by Boehringer Mannheim Corporation) and has been used in pregnant mice at a dose of 400 nMoles (0.44 mg) with any detectable toxicity in the dams or their progeny.[156] FDA approval has been obtained for experimental use in humans on at least one cationic amphiphilic compound in humans, as a DNA transfection agent.[157,158] Thus, these compounds are effectively tolerated, safe, and will, importantly, protect experimental animals against the lethal effects of endotoxin.

SUMMARY AND CONCLUSIONS OF EXAMPLES 1–10

The experimental data that we have obtained thus establish that cationic amphiphilic substances with structural features as outlined earlier and present in such molecules as DOSPER possess value not only as nontoxic endotoxin-sequestering agents in vitro, and in vivo, but may also be effective in preventing the deleterious consequences of cytokine release induced by Gram-positive organisms, and may therefore find applications in the low cost, yet effective treatment or prophylaxis of sepsis and other disease states related to cytokine overproduction caused by bacteria or bacterial products.

References Cited

1. Balk, R. A. and R. C. Bone. 1989. The septic syndrome. Definition and clinical implications. *Crit. Care Clin.* 5:1–8.
2. Bone, R. C. 1996. The sepsis syndrome. Definition and general approach to management. *Clin. Chest Med.* 17:175–181.
3. Hamill, R. J. and D. G. Maki. 1984. Endotoxin shock in man caused by gram-negative bacillietiology, clinical features, diagnosis, natural history and prevention. In Handbook of Endotoxin. (Clinical Aspects of Endotoxic Shock). R. A. Proctor, editor. Elsevier Publications, Amsterdam. 55–114.
4. Bucklin, S. E., Y. Fujihara, M. C. Leeson, and D. C. Morrison. 1994. Differential antibiotic-induced release of endotoxin from gram-negative bacteria. *Eur. J. Clin. Microbiol. Infect. Dis.* 13 Suppl. 1:43–51.
5. Prins, J. M., S. J. H. Van Deventer, E. J. Kuijper, and P. Speelman. 1994. Clinical relevance of antibiotic-induced endotoxin release. *Antimicrob. Agents Chemother.* 38:1211–1218.
6. Prins, J. M., M. A. van Agtmael, E. J. Kuijper, S. J. van Deventer, and P. Speelman. 1995. Antibiotic-induced endotoxin release in patients with gram-negative urosepsis: a double-blind study comparing imipenem and ceftazidime. *J. Infect. Dis.* 172:886–891.
7. Hurley, J. C. 1995. Antibiotic-induced release of endotoxin. A therapeutic paradox. *Drug Saf.* 12:183–195.
8. Lüderitz, O., C. Galanos, and E. T. Rietschel. 1982. Endotoxins of gram-negative bacteria. *Pharmacol. Ther.* 15:383–402.
9. Raetz, C. R. H. 1990. Biochemistry of Endotoxins. *Annu. Rev. Biochem.* 59:129–170.
10. Morrison, D. C. and J. L. Ryan. 1987. Endotoxins and disease mechanisms. *Annu. Rev. Med.* 38:417–432.
11. Rietschel, E. T., T. Kirikae, F. U. Schade, U. Mamat, G. Schmidt, H. Loppnow, A. J. Ulmer, U. Zähringer, U. Seydel, F. Di Padova, M. Schreier, and H. Brade. 1994. Bacterial endotoxin: Molecular relationships of structure to activity and function. *FASEB J.* 8:217–225.
12. Evans, T. J. 1996. The role of macrophages in septic shock. Immunobiology 195:655–659.
13. Knox, K. W. 1966. The relation of 3-deoxy-2-oxo-octonate to the serological and physical properties of a lipopolysaccharide from a rough strain of *Escherichia coli*. *Biochem. J.* 100:73–78.
14. Mayer, H., U. R. Bhat, H. Masoud, J. Radziejewska-Lebrecht, C. Widemann, and J. H. Krauss. 1989. Bacterial lipopolysaccharides. *Pure & Appl. Chem.* 61:1271–1282.
15. Young, L. S. 1991. Endotoxins and mediators—An introduction. In Bacterial Endotoxins: Cytokine Mediators and New Therapies for Sepsis. A. Sturk, editor. Wiley-Liss.Inc. 1–7.
16. Loppnow, H., H.-D. Flad, E. T. Rietschel, and H. Brade. 1993. The Active Principle of Bacterial Lipopolysaccharide (Endotoxin) for Cytokine Induction. In Pathophysiology of Shock, Sepsis, and Organ Failure. G. Schlag and H. Redi, editors. Springer Verlag, berlin, Heidelberg, New York. 405–416.
17. Sundaresan, R. and J. N. Sheagren. 1995. Current understanding and treatment of sepsis. *Complications Surg.* 14:261–268.
18. Lefer, A. M. 1994. Endotoxin, cytokines, and nitric oxide in shock [editorial]. *Shock* 1:79–80.
19. Loppnow, H., H. Brade, E. T. Rietschel, and H. D. Flad. 1994. Induction of cytokines in mononuclear and vascular cells by endotoxin and other bacterial products. *Methods Enzymol.* 236:3–10.
20. Wright, R. M., C. S. Holladay, and B. L. Spangelo. 1993. Lipopolysaccharide induces interleukin-6 release from rat peritoneal macrophages in vitro: Evidence for a novel mechanism. *Circ. Shock* 41:131–137.
21. Dendorfer, U., P. Oettgen, and T. A. Libermann. 1994. Multiple regulatory elements in the interleukin-6 gene mediate induction by prostaglandins, cyclic AMP, and lipopolysaccharide. *Mol. Cell Biol.* 14:4443–4454.
22. Xing, Z., M. Jordana, H. Kirpalani, K. E. Driscoll, T. J. Schall, and J. Gauldie. 1994. Cytokine expression by neutrophils and macrophages in vivo: endotoxin induces tumor necrosis factor-alpha, macrophage inflammatory protein-2, interleukin-1 beta, and interleukin-6 but not RANTES or transforming growth factor-beta 1 mRNA expression in acute lung inflammation [published erratum appears in Am J. Respir Cell Mol Biol 1994 Mar;10(3): following 346]. *Am. J. Respir. Cell Mol. Biol.* 10:148–153.
23. Ozman, L., M. Pericin, J. Hakimi, R. A. Chizzonite, M. Wysocka, G. Trinchieri, M. Gately, and G. Garotta. 1994. Interleukin 12, interferon gamma, and tumor necrosis factor $\alpha$ are the key cytokines of the generalized Schwartzman reaction. *J. Exp. Med.* 180:907–916.
24. Schade, U. F., R. Engel, and D. Jakobs. 1991. The role of lipoxygenases in endotoxin-induced cytokine production. In Bacterial Endotoxins: Cytokine Mediators and New Therapies for Sepsis. A. Sturk, editor. Wiley-Liss.Inc. 73–82.
25. Akarasereenont, P., E. Hide, P. Ney, C. Thiemermann, and J. R. Vane. 1995. The induction of cyclooxygenase-2 elicited by endotoxin in endothelial cells and macrophages is inhibited by prostaglandin E1 and 13,14-dihydro prostaglandin E1. *Agents Actions Suppl.* 45:59–64.
26. Watanabe, S., T. Kobayashi, and H. Okuyama. 1994. Regulation of lipopolysaccharide-induced tumor necrosis factor alpha production by endogenous prostaglandin E2 in rat resident and thioglycollate-elicited macrophages. *J. Lipid Mediat. Cell Signal.* 10:283–294.
27. Hempel, S. L., M. M. Monick, and G. W. Hunninghake. 1994. Lipopolysaccharide induces prostaglandin H synthase-2 protein and mRNA in human alveolar macrophages and blood monocytes. *J. Clin. Invest.* 93:391–396.
28. Hagmann, W., C. Denzlinger, and D. Keppler. 1985. Production of peptide leukotrienes in endotoxin shock. (*FEBS*) 180:309–313.
29. Chen, X. S., J. R. Sheller, E. N. Johnson, and C. D. Funk. 1994. Role of leukotrienes revealed by targeted disruption of the 5-lipoxygenase gene. *Nature* 372:179–182.
30. Camussi, G., F. Mariano, L. Biancone, A. De Martino, B. Bussolati, G. Montrucchio, and P. S. Tobias. 1995. Lipopolysaccharide binding protein and CD14 modulate the synthesis of platelet-activating factor by human monocytes and mesangial and endothelial cells stimulated with lipopolysaccharide. *J. Immunol.* 155:316–324.
31. Ruggiero, V., C. Chiapparino, S. Manganello, L. Pacello, P. Foresta, and E. A. Martelli. 1994. Beneficial effects of a novel platelet-activating factor receptor antagonist, ST 899, on endotoxin-induced shock in mice. *Shock* 2:275–280.
32. Bozza, P. T., H. C. Castro Faria Neto, A. R. Silva, A. P. Larangeira, P. M. Silva, M. A. Martins, and R. S. Cordeiro. 1994. Lipopolysaccharide-induced pleural neutrophil accumulation depends on marrow neutrophils and platelet-activating factor. *Eur. J. Pharmacol.* 270:143–149.
33. Donovan Peluso, M., L. D. George, and A. C. Hassett. 1994. Lipopolysaccharide induction of tissue factor 33. expression in THP-1 monocytic cells. Protein-DNA interactions with the promoter. *J. Biol. Chem.* 269:1361–1369.
34. Levi, M., H. ten Cate, K. A. Bauer, T. van der Poll, T. S. Edgington, H. R. Buller, S. J. van Deventer, C. E. Hack, J. W. ten Cate, and R. D. Rosenberg. 1994. Inhibition of endotoxin-induced activation of coagulation and fibrinolysis by pentoxifylline or by a monoclonal anti-tissue factor antibody in chimpanzees. *J. Clin. Invest* 93:114–120.
35. Meyer, J. and D. L. Traber. 1992. Nitric oxide and endotoxin shock. *Cardiovasc. Res.* 26:558
36. Fahmi, H., D. Charon, M. Mondagne, and R. Chaby. 1995. Endotoxin-induced desensitization of mouse macrophages is mediated in part by nitric oxide production. *Infect. Immun.* 63:1863–1869.
37. Heinemann, A. and R. E. Stauber. 1995. The role of inducible nitric oxide synthase in vascular hyporeactivity of endotoxin-treated and portal hypertensive rats. *Eur. J. Pharmacol.* 278:87–90.
38. Schmidlin, A. and H. Wiesinger. 1995. Stimulation of arginine transport and nitric oxide production by lipopolysaccharide is mediated by different signaling pathways in astrocytes. *J. Neurochem.* 65:590–594.
39. Wang, J. F., Y. Q. Gao, H. Lippton, A. Hyman, and J. J. Spitzer. 1994. The roles of nitric oxide and hydrogen peroxide production in lipopolysaccharide-induced intestinal damage. *Shock* 2:185–191.
40. Parrillo, J. E. 1993. Pathogenic mechanisms of septic shock. *New Engl. J. Med.* 328:1471–1477.
41. Henricson, B. E., C. L. Manthey, P. Y. Perera, T. A. Hamilton, and S. N. Vogel. 1993. Dissociation of lipopolysaccharide (LPS)-inducible gene expression in murine macrophages pretreated with smooth LPS versus monophosphoryl lipid A. *Infect. Immun.* 61:2325–2333.
42. Brandtzaeg, P. 1996. Significance and pathogenesis of septic shock. *Curr. Top. Microbiol. Immunol.* 216:15–37.
43. Crowley, S. R. 1996. The pathogenesis of septic shock. *Heart Lung* 25:124–134.
44. Shenep, J. L. 1996. Septic shock. *Adv. Pediatr. Infect. Dis.* 12:209–241.
45. Thijs, L. G., A. B. Groeneveld, and C. E. Hack. 1996. Multiple organ failure in septic shock. *Curr. Top. Microbiol. Immunol.* 216:209–237.
46. Vincent, J. L. 1996. Definition and pathogenesis of septic shock. *Curr. Top. Microbiol. Immunol.* 216:1–13.
47. Bone, R. C. 1993. Gram-negative sepsis: a dilemma of modern medicine. *Clin. Microbiol. Rev.* 6:57–68.
48. Bone, R. C., C. J. Fisher, T. P. Clemmer, and et al. 1987. A controlled clinical trial of high-dose methylprednisolone in the treatment of severe sepsis and septic shock. *N. Engl. J. Med.* 317:653
49. Hinshaw, L. B. and Veterans Administration Study Group. 1987. Effect of high-dose glucocorticoid therapy on mortality in patients with clinical signs of systemic sepsis. *N. Engl. J. Med.* 217:659
50. Le Roy, D., P. Morand, S. Lengacher, M. Celio, G. E. Grau, M. P. Glauser, and D. Heumann. 1996. *Streptococcus mitis* cell walls and lipopolysaccharide induce lethality in D-galactosamine-sensitized mice by a tumor necrosis factor-dependent pathway. *Infect. Immun.* 64:1846–1849.
51. Hinshaw, L. B., T. E. Emerson,Jr., F. B. Taylor,Jr., A. C. Chang, M. Duerr, G. Peer, D. J. Flournoy, G. L. White, S. D. Kosanke, C. K. Murray, and et al. 1992. Lethal *Staphylococcus aureus*-induced shock in primates: prevention of death with anti-TNF antibody. *J. Trauma* 33:568–573.
52. Freudenberg, M. A. and C. Galanos. 1991. Tumor necrosis factor alpha mediates lethal activity of killed Gram-negative abd Gram-positive bacteria in D-galactosamine-treated mice. *Infect. Immun.* 59:2110–2115.
53. Wayte, J., A. T. Silva, T. Krausz, and J. Cohen. 1993. Observations on the role of tumor necrosis factor-alpha in a murine model of shock due to *Streptococcus pyogenes*. *Crit. Care Med.* 21:1207–1212.
54. Aiura, K., J. A. Gelfand, J. F. Burke, R. C. Thompson, and C. A. Dinarello. 1993. Interleukin-1 (IL-1) receptor antagonist prevents Staphylococcus epidermidis-induced hypotension and reduces circulating levels of tumor necrosis factor and IL-1 beta in rabbits. *Infect. Immun.* 61:3342–3350.
55. Tracey, K. J., Y. Fong, D. G. Hesse, K. R. Manogue, A. T. Lee, G. C. Kuo, S. F. Lowry, and A. Cerami. 1987. Anti-cachectin/TNF monoclonal antibodies prevent septic shock during lethal bacteremia. *Nature* 330:662–664.
56. Heumann, D., C. Barras, A. Severin, M. P. Glauser, and A. Tomasz. 1994. Gram-positive cell walls stimulate synthesis of tumor necrosis factor alpha and interleukin-6 by human monocytes. *Infect. Immun.* 62:2715–2721.
57. Bayston, K., M. Tomlinson, and J. Cohen. 1992. In-vitro stimulation of TNF-alpha from human whole blood by cell-free supernatants of gram-positive bacteria. *Cytokine.* 4:397–402.
58. Hunolstein, C., A. Totolian, G. Alfarone, G. Mancuso, V. Cusumano, G. Teti, and G. Orefici. 1997. Soluble antigens from group B streptococci induce cytokine production in human blood cultures. *Infect. Immun.* 65:4017–4021.
59. Soto, A., T. J. Evans, and J. Cohen. 1996. Proinflammatory cytokine production by human peripheral blood mononuclear cells stimulated with cell-free supernatants of viridans streptococci. *Cytokine* 8:300–304.
60. Bone, R. C. 1993. How gram-positive organisms cause sepsis. *J. Crit. Care* 8:51–59.
61. Kragsbjerg, P., H. Holmberg, and T. Vikerfors. 1996. Dynamics of blood cytokine concentrations in patients with bacteremic infections. *Scand. J. Infect. Dis.* 28:391–398.
62. Baud, L., J. Cadranel, G. Offenstadt, L. Luquel, B. Guidet, and P. Amstutz. 1990. Tumor necrosis factor and septic shock. *Crit. Care Med.* 18:349–350.
63. Henderson, B. and M. Wilson. 1996. Cytokine induction by bacteria: beyond lipopolysaccharide. *Cytokine* 8:269–282.
64. Renzi, P. M. and C.-H. Lee. 1995. A comparative study of biological activities of lipoteichoic acid and lipopolysaccharide. *J. Endotoxin Res.* 2:431–441.
65. Bhakdi, S., T. Klonisch, P. Nuber, and W. Fischer. 1991. Stimulation of monokine production by lipoteichoic acid. *Infect. Immun.* 59:4614–4620.
66. Fischer, W., T. Mannsfeld, and G. Hagen. 1990. On the basic structure of poly(glycerophosphate) lipoteichoic acids. *Biochem. Cell. Biol.* 68:33–43.
67. Suda, Y., H. Tochio, K. Kawano, H. Takada, T. Yoshida, S. Kotani, and S. Kusumoto. 1995. Cytokine-inducing glycolipids in the lipoteichoic acid fraction from *Enterococcus hirae* ATCC 9790. *FEMS Immunol. Med. Microbiol.* 12:97–112.
68. Kusunoki, T., E. Hailman, T. S.-C. Juann, H. S. Lichenstein, and S. D. Wright. 1995. Molecules from *Staphylococcus aureus* that bind CD14 and stimulate innate immune response. *J. Exp. Med.* 182:1673–1682.
69. Hashimoto, M., J.-I. Yasuoka, Y. Suda, H. Takada, T. Yoshida, S. Kotani, and S. Kusumoto. 1997. Structural 69. feature of the major but not cytokine-inducing molecular species of lipoteichoic acid. *J. Biochem. Tokyo* 121:779–786.
70. Abraham, E. 1997. Therapies for sepsis. Emerging therapies for sepsis and septic shock. *West. J. Med.* 166:195–200.
71. Ognibene, F. P. 1997. Pathogenesis and innovative treatment of septic shock. *Adv. Intern. Med.* 42:313–338.
72. Aydintug, M. K., T. J. Inzana, T. Letonja, W. C. Davis, and L. B. Corbeil. 1989. Cross-Reactivity of Monoclonal Antibodies to *Eschericha coli* J5 with Heterologous Gram-negative Bacteria and Extracted Lipopolysaccharides. *J. Infect. Dis.* 160–5:846–857.(Abstr.)
73. Pollack, M., J. K. S. Chia, N. L. Koles, M. Miller, and G. Guelde. 1989. Specificity and cross-reactivity of monoclonal antibodies reactive with the core and lipid A regions of bacterial lipopolysaccharide. *J. Infect. Dis.* 159:168–188.
74. Terashima, M., I. Uezumi, T. Tomio, M. Kato, K. Irie, T. Okuda, S.-I. Yokota, and H. Noguchi. 1991. A protective human monoclonal antibody directed to the outer core region of *pseudomonas aeruginosa* lipopolysaccharide. *Infect. Immun.* 59/1:1–6.
75. Ziegler, E. J., C. J. Fisher,Jr., C. L. Sprung, R. C. Straube, J. C. Sadoff, G. E. Foulke, C. H. Wortel, M. P. Fink, R. P. Dellinger, N. N. H. Teng, I. E. Allen, H. J. Berger, G. L. Knatterud, A. F. LoBuglio, C. R. Smith, and HA-1A Sepsis Study Group. 1991. Treatment of gram-negative bacteremia and septic shock with HA-1A human monoclonal antibody against endotoxin—A randomized, double-blind, placebo-controlled trial. *N. Engl. J. Med.* 324:429–436.
76. Goto, M., W. P. Zeller, R. M. Hurley, J. S. Jong, and C.-H. Lee. 1991. Prophylaxis and treatment of newborn endotoxic shock with anti-lipid A monoclonal antibodies. *Circ. Shock* 35:60–64.
77. Greenberg, R. N., K. M. Wilson, A. Y. Kunz, N. I. Wedel, and K. J. Gorelick. 1991. Randomized, double-blind phase II study of anti-endotoxin antibody (E5) as adjuvant therapy in humans with serious Gram-negative infections. In Bacterial Endotoxins: Cytokine Mediators and New Therapies for Sepsis. Anonymous Wiley-Liss, Inc. 179–186.
78. Wortel, C. H., E. J. Ziegler, and S. J. H. Van Deventer. 1991. Therapy of Gram-negative sepsis in man with anti-endotoxin antibodies: A review. In Bacterial Endotoxins: Cytokine Mediators and New Therapies for Sepsis. A. Sturk, editor. Wiley-Liss. Inc. 161–178.
79. McCabe, W. R. 1992. Antibody to endotoxin in the treatment of gram-negative sepsis. *JAMA* 267:2325
80. Di Padova, F. E., V. Mikol, G. R. Barclay, I. R. Poxton, H. Brade, and E. T. Rietschel. 1994. Anti-lipopolysaccharide core antibodies. In Bacterial endotoxins: Basic science to anti-sepsis strategies. J. Levin, S. J. H. v.Deventer, T. v.d.Poll, and A. Sturk, editors. Wiley-Liss, Inc. New York. 85–94.
81. Siegel, J. P. 1995. Antiendotoxin antibodies. *Ann. Intern. Med.* 122:315
82. Ziegler, E. J., J. A. McCutchan, J. Fierer, M. P. Glauser, J. C. Sadoff, H. Douglas, and A. I. Braude. 1982. Treatment of gram-negative bacteremia and shock with human antiserum to a mutant *Escherichia coli*. *N. Engl. J. Med.* 307:1225–1230.
83. Baumgartner, J. D., M. P. Glauser, J. A. McCutchan, E. J. Ziegler, G. van Melle, M. R. Klauber, M. Vogt, E. Muehlen, R. Luethy, R. Chiolero, and et al. 1985. Prevention of gram-negative shock and death in surgical patients by antibody to endotoxin core glycolipid. *Lancet* 2:59–63.
84. Griesman, S. E. and C. A. Johnston. 1997. Evidence against the hypothesis that antibodies to the inner core of lipopolysaccharides in antisera raised by immunization with enterobacterial deep-rough mutants confer broad-spectrum protection during Gram-negative bacterial sepsis. *J. Endotoxin. Res.* 4:123–153.
85. Ziegler, E. J. 1988. Protective antibody to endotoxin core: The emperor's new clothes? *J. Infect. Dis.* 158:286–290.
86. Wenzel, R. P. 1992. Anti-endotoxin monoclonal antibodies—A second look. *N. Engl. J. Med.* 326:1151–1153.
87. Weil, M. H. 1994. Lessons learned from clinical trials on monoclonal anti-endotoxin antibody. *Arch. Intern. Med.* 154:1183–1184.
88. Cross, A. S. 1994. Antiendotoxin antibodies: A dead end. *Ann. Intern. Med.* 121:58–60.
89. Cross, A. S. and S. Opal. 1994. Therapeutic intervention in sepsis with antibody to endotoxin: Is there a future? *J. Endotoxin. Res.* 1:57–69.
90. Weil, M. H. 1994. Lessons learned from clinical trials on monoclonal anti-endotoxin antibody [editorial; comment]. *Arch. Intern. Med.* 154:1183
91. Hoess, A., S. Watson, G. R. Siber, and R. Liddington. 1993. Crystal structure of an endotoxin-neutralizing protein from the horseshoe crab, Limulus anti-LPS factor, at 1.5 Å resolution. *EMBO J.* 12:3351–3356.
92. Schumann, R. R., N. Lamping, C. Kirschning, H.-P. Knopf, A. Hoess, and F. Herrmann. 1994. Lipopolysaccharide binding protein: Its role and therapeutical potential in inflammation and sepsis. *Biochem. Soc. Trans.* 22:80–82.
93. Evans, T. J., A. Carpenter, D. Moyes, R. Martin, and J. Cohen. 1995. Protective effects of a recombinant amino-terminal fragment of human Bactericidal/Permeability-increasing protein in an animal model of gram-negative sepsis. *J. Infect Dis.* 171:153–160.
94. von der Mohlen, M. A., S. J. van Deventer, M. Levi, B. van den Ende, N. I. Wedel, B. J. Nelson, N. Friedmann, and J. W. ten Cate. 1995. Inhibition of endotoxin-induced activation of the coagulation and fibrinolytic pathways using a recombinant endotoxin-binding protein (rBPI23). *Blood* 85:3437–3443.
95. von der Möhlen, M. A. M., N. Kimmings, N. I. Wedel, M. L. C. M. Mevissen, J. Jansen, N. Friedmann, T. J. Lorenz, B. J. Nelson, M. L. White, R. Bauer, C. E. Hack, A. J. M. Eerenberg, and S. J. H. Van Deventer. 1995. Inhibition of endotoxin-induced cytokine release and neutrophil activation in humans by use of recombinant bectericidal/permeability-increasing protein. *J. Infect. Dis.* 171:144–151.
96. Appelmelk, B. J., Y.-Q. An, B. G. Thijs, D. M. MacLaren, and J. De Graaff. 1994. Recombinant human bactericidal/permeability-increasing protein (rBPI$_{23}$) is a universal lipopolysaccharide-binding ligand. *Infect. Immun.* 62:3564–3567.
97. Corradin, S. B., D. Heumann, P. Gallay, J. Smith, J. Mauel, and M. P. Glauser. 1994. Bactericidal/permeability-increasing protein inhibits induction of macrophage nitric oxide production by lipopolysaccharide. *J. Infect. Dis.* 169:105–111.
98. Elsbach, P. 1994. Bactericidal permeability-increasing protein in host defence against gram-negative bacteria and endotoxin. *Ciba. Found. Symp.* 186:176–187.
99. Fisher, C. J., Jr., M. N. Marra, J. E. Palardy, C. R. Marchbanks, R. W. Scott, and S. M. Opal. 1994. Human neutrophil bactericidal/permeability-increasing protein 99. reduces mortality rate from endotoxin challenge: A placebo-controlled study. *Crit. Care Med.* 22:553–558.
100. Weersink, A. J. L. 1994. BPI: more than an intracellular LPS-binding protein of human neutrophils. 13 p.
101. Wilde, C. G., J. J. Seilhamer, M. McGrogan, N. Ashton, J. L. Snable, J. C. Lane, S. R. Leong, M. 13. Thornton, K. L. Miller, R. W. Scott, and M. N. Marra. 1994. Bactericidal/permeability-increasing protein and lipopolysaccharide (LPS)-binding protein. LPS binding properties and effects on LPS-mediated cell activation. *Journal of Biological Chemistry* 269:17411–17416.
102. Gazzano-Santoro, H., J. B. Parent, L. Grinna, A. Horwitz, T. Parsons, G. Theofan, P. Elsbach, J. Weiss, and P. J. Conlon. 1992. High-Affinity Binding of the Bactericidal/Permeability-Increasing Protein and a Recombinant Amino-Terminal Fragment to the Lipid A Region of Lipopolysaccharide. *Infection and Immunity* 60:4754–4761.
103. Elsbach, P., J. Weiss, R. C. Franson, S. Beckerdite-Quagliata, A. Schneider, and L. Harris. 1979. Separation and Purification of a Potent Bactericidal/Perneability-increasing Protein and a Closely Associated Phospholipase $A_2$ from Rabbit Polymorphonuclear Leukocytes. *Journal of Biological Chemistry* 254:11000–11009.
104. Kohler, G., U. Hering, O. Zschornig, and K. Arnold. 1997. Annexin V interaction with phosphatidylserine-containing vesicles at low and neutral pH. *Biochemistry* 36:8189–8194.
105. Bandorowicz Pikula, J., A. F. Sikorski, K. Bialkowska, and A. Sobota. 1996. Interaction of annexins IV and VI with phosphatidylserine in the presence of Ca2+: monolayer and proteolytic study. *Mol. Membr. Biol.* 13:241–250.
106. Mukhopadhyay, S. and W. Cho. 1996. Interactions of annexin V with phospholipid monolayers. *Biochim. Biophys. Acta* 1279:58–62.
107. Luecke, H., B. T. Chang, W. S. Mailliard, D. D. Schlaepfer, and H. T. Haigler. 1995. Crystal structure of the annexin XII hexamer and implications for bilayer insertion [see comments]. *Nature* 378:512–515.
108. Goossens, E. L., C. P. Reutelingsperger, F. H. Jongsma, R. Kraayenhof, and W. T. Hermens. 1995. Annexin V perturbs or stabilises phospholipid membranes in a calcium-dependent manner. *FEBS Lett.* 359:155–158.
109. Zähringer, U., B. Lindner, and E. T. Rietschel. 1994. Molecular structure of lipid A, the endotoxic center of bacterial lipopolysaccharides. *Adv. Carbohydr. Chem. Biochem.* 50:211–276.
110. Rietschel, E. T., T. Kirikae, U. F. Schade, A. J. Ulmer, 0. Holst, H. Brade, G. Schmidt, U. Mamat, H.-D. Grimmecke, S. Kusumoto, and U. Zähringer. 1993. The chemical structure of bacterial endotoxin in relation to bioactivity. *Immunobiol.* 187:169–190.
111. Rietschel, E. T. and H. Brade. 1992. Bacterial Endotoxins. *Sci. Am.* 267:54–61.
112. Rietschel, E. T., T. Kirikae, W. Feist, H. Loppnow, P. Zabel, L. Brade, A. J. Ulmer, H. Brade, U. Seydel, U. Z ähringer, M. Schlaak, H.-D. Flad, and U. Schade. 1991. Molecular aspects of the chemistry and biology of endotoxin. 42. *Colloquium Mosbach, Molecular Aspects of Inflammation* 207–231.
113. David, S. A., P. Balaram, and V. I. Mathan. 1995. Characterization of the interaction of lipid A and lipopolysaccharide with human serum albumin: implications for an endotoxin-carrier function for albumin. *J. Endotoxin. Res.* 2:99–106.
114. Ohno, N. and D. C. Morrison. 1989. Lipopolysaccharide interaction with lysozyme. Binding of lipopolysaccharide to lysozyme and inhibition of lysozyme enzymatic activity. *J. Biol. Chem.* 264:4434–4441.
115. Takada, K., N. Ohno, and T. Yadomae. 1994. Detoxification of lipopolysaccharide (LPS) by egg white lysozyme. *FEMS Immunol. Med. Microbiol.* 9:255–264.
116. Ohno, N. 1992. LPS binding proteins in granulocyte lysosomes. In Bacterial endotoxic lipopolysaccharides Volume I Molecular biochemistry and cellular biology. D. C. Morrison and J. L. Ryan, editors. CRC Press, Boca Raton. 387–404.
117. Ohno, N., N. Tanida, and T. Yadomae. 1991. Characterization of complex formation between lipopolysaccharide and lysozyme. *Carbohydr. Res.* 214:115–130.
118. Takada, K., N. Ohno, and T. Yadomae. 1994. Binding of lysozyme to lipopolysaccharide suppresses tumor necrosis factor production in vivo. *Infect. Immun.* 62:1171–1175.
119. David, S. A., V. I. Mathan, and P. Balaram. 1992. Interaction of melittin with endotoxic lipid A. *Biochim. Biophys. Acta* 1123:269–274.
120. David, S. A., K. A. Balasubramanian, V. I. Mathan, and P. Balaram. 1992. Analysis of the binding of polymyxin B to endotoxic lipid A and core glycolipid using a fluorescent displacement probe. *Biochim. Biophys. Acta* 1165:147–152.
121. David, S. A., P. Balaram, and V. I. Mathan. 1993. Interaction of basic amphiphilic polypeptide antimicrobials, gramicidin S, tyrocidin and efrapeptin, with endotoxic lipid A. *Med. Microbiol. Lett.* 2:42–47.
122. David, S. A., S. Bhattacharjya, V. I. Mathan, and P. Balaram. 1994. Elucidation of the conformation of free and LPS-bound polymyxin B nonapeptide in water by 2D-NMR and restrained molecular dynamics methods and molecular modeling of polymyxin-lipid A complex. *J. Endotoxin. Res.* 1(suppl):A60
123. David, S. A., B. Bechtel, C. Annaiah, V. I. Mathan, and P. Balaram. 1994. Interaction of cationic amphiphilic drugs with lipid A: Implications for development of endotoxin antagonists. *Biochim. Biophys. Acta Lipids Lipid Metab.* 1212:167–175.
124. David, S. A., V. I. Mathan, and P. Balaram. 1995. Interactions of linear dicationic molecules with lipid A: Structural requisites for optimal binding affinity. *J. Endotoxin. Res.* 2:325–336.
125. David, S. A. 1995. Analysis of the desirable structural properties in potential endotoxin antagonists. Ph.D.
126. David, S. A., V. I. Mathan, and P. Balaram. 1995. Interactions of linear dicationic molecules with lipid A: Structural features that correspond to optimal binding affinity. *J. Endotoxin. Res.* 2:325–336.
127. Solodin, I., C. S. Brown, M. S. Bruno, C.-Y. Chow, E.-H. Jang, R. J. Debs, and T. D. Heath. 1995. A novel series of amphiphilic imidazolinium compounds for invitro and in vivo gene delivery. *Biochemistry* 34:13537–13544.
128. Behr, J.-P., B. Demeneix, J.-P. Loeffler, and J. Perez-Mutul. 1989. Efficient gene transfer into mammalian primary endocrine cells with lipopolyamine-coated DNA. *Proc. Natl. Acad. Sci. USA* 86:6982–6986.
129. Behr, J.-P. 1994. Gene transfer with synthetic cationic amphiphiles: Prospects for gene therapy. *Bioconjug. Chem.* 5:382–389.
130. Gao, X. and L. Huang. 1995. Cationic liposome-mediated gene transfer. *Gene Therapy* 2:710–722.
131. Leventis, R. and J. R. Silvius. 1990. Interactions of mammalian cells with lipid dispersions containing novel metabolizable cationic amphiphiles. *Biochim. Biophys. Acta* 1023:124–132.

132. Xu, Y. and F. C. J. Szoka. 1996. Mechanism of DNA release from cationic liposome/DNA complexes used in cell transfection. *Biochemistry* 35:5616–5623.
133. Felgner, P. L., T. R. Gadek, M. Holm, R. Roman, H. W. Chan, M. Wenz, J. P. Northrop, G. M. Ringold, and M. Danielsen. 1987. Lipofection: a highly efficient, lipid-mediated DNA transfection procedure. *Proc. Natl. Acad. Sci. USA* 84:7413–7417.
134. Morrison, D. C. and D. M. Jacobs. 1976. Binding of polymyxin B to the lipid A portion of bacterial lipopolysaccharides. *Immunochemistry* 13:813–818.
135. Stokes, D. C., J. L. Shenep, M. L. Fishman, W. K. Hidner, G. K. Bysani, and K. Rufus. 1989. Polymyxin B prevents lipopolysaccharide-induced release of tumor necrosis factor- from alveolar macrophages. *J. Infect. Dis.* 160:52–57.
136. Tanaka, S. and S. Iwanaga. 1993. Limulus test for detecting bacterial endotoxins. *Methods Enzymol.* 223:358–364.
137. Muta, T., F. Tokunaga, T. Nakamura, T. Morita, and S. Iwanaga. 1993. Limulus clotting factor C: Lipopolysaccharide-sensitive serine protease zymogen. *Methods Enzymol.* 223:336–345.
138. Green et al. 1982. Analysis of nitrate, nitrite and [15-N] nitrate in biological fluids. *Anal. Biochem.* 126:131
139. Shakov, A. N., M. A. Collart, P. Vassalli, S. A. Nedospasov, and C. V. Jongeneel. 1990. kappa-B-type enhancers are involved in lipopolysaccharide-mediated transcriptional activation of tumor necrosis factor alpha gene in primary macrophages. *J. Exp. Med.* 171:35–47.
140. Biragyn, A. and S. A. Nedospasov. 1995. Lipopolysaccharide-induced expression of TNF-alpha gene in the macrophage cell line ANA-1 is regulated at the level of transcription processivity. *J. Immunol.* 155:674–683.
141. Takashiba, S., L. Shapira, S. Amar, and T. E. van Dyke. 1993. Cloning and characterization of the human TNF-alpha promoter region. *Gene* 131:307–308.
142. Zheng, S., M. C. Brown, and S. M. Taffet. 1993. Lipopolysaccharide stimulates both nuclear localization of the nuclear factor kappa-B 50 kDa subunit and loss of the 105 kDa precursor in RAW264 macrophage-like cells. *J. Biol. Chem.* 268:17233–17239.
143. Ray, A., M. Hannink, and B. K. Ray. 1995. Concerted participation of NF-kappa B and C/EBP heteromer in lipopolysaccharide induction of serum amyloid A gene expression in liver. *J. Biol. Chem.* 270:7365–7374.
144. Ishikawa, Y., N. Mukaida, K. Kuno, N. Rice, S. Okamoto, and K. Matsushima. 1995. Establishment of lipopolysaccharide-dependent nuclear factor kappa B activation in a cell-free system. *J. Biol. Chem.* 270:4158–4164.
145. Oeth, P. A., G. C. Parry, C. Kunsch, P. Nantermet, C. A. Rosen, and N. Mackman. 1994. Lipopolysaccharide induction of tissue factor gene expression in monocytic cells is mediated by binding of c-Rel/p65 heterodimers to a kappa B-like site. *Mol. Cell Biol.* 14:3772–3781.
146. Silverstein, R., C. A. Christoffersen, and D. C. Morrison. 1989. Modulation of endotoxin lethality in mice by hydrazine sulfate. *Infect. Immun.* 57:2072–2078.
147. Silverstein, R., B. R. Turley, C. A. Christoffersen, D. C. Johnson, and D. C. Morrison. 1991. Hydrazine sulfate protects D-galactosamine-sensitized mice against endotoxin and tumor necrosis factor/cachectin lethality: Evidence of a role for the pituitary. *J. Exp. Med.* 173:357–365.
148. Silverstein, R., M. Norimatsu, and D. C. Morrison. 1997. Fundamental differences during Gram-positive versus Gram-negative sepsis become apparent during bacterial challenge of D-galactosamine-treated mice. *J. Endotoxin. Res.* 4:173–181.
149. Galanos, C., O. Lüderitz, E. T. Rietschel, O. Westphal, H. Brade, L. Brade, M. A. Freudenberg, U. F. Schade, M. Imoto, S. Yoshimura, S. Kusumoto, and T. Shiba. 1985. Synthetic and natural *Escherichia coli* free lipid A express identical endotoxic activities. *Eur. J. Biochem.* 148:1–5.
150. Galanos, C., V. Lehmann, O. Lüderitz, E. T. Rietschel, O. Westphal, H. Brade, L. Brade, M. A. Freudenberg, T. Hansen-Hagge, T. Lüderitz, G. McKenzie, U. Schade, W. Strittmatter, K. Tanamoto, U. Zähringer, M. Imoto, M. Yamamoto, T. Shimamoto, S. Kusumoto, and T. Shiba. 1984. Endotoxic properties of chemically synthesized lipid A part structures: Comparison of synthetic lipid A precursor and synthetic analogues with biosynthetic lipid A precursor and free lipid A. *Eur. J. Biochein.* 140:221–227.
151. Galanos, C., M. A. Freudenberg, and W. Reutter. 1979. Galactosamine-induced sensitization to the lethal effects of endotoxin. *Proc. Natl. Acad. Sci. USA* 76(11):5939–5943.
152. Bucklin, S. E. and D. C. Morrison. 1995. Differences in therapeutic efficacy among cell wall-active antibiotics in a mouse model of Gram-negative sepsis. *J. Infect. Dis.* 172:1519–1527.
153. Vaara, M. and T. Vaara. 1983. Polycations sensitize enteric bacteria to antibiotics. *Antimicrobial Agents and Chemotherapy* 24:107–113.
154. Vaara, M. and T. Vaara. 1983. Polycations as outer membrane disorganizing agents. *Antimicrobial Agents and Chemotherapy* 24:114–122.
155. Vukajlovich, S. W. 1986. Antibody-independent activation of the classical pathway of human serum complement by lipid A is restricted to Re-chemotype lipopolysaccharide and purified lipid A. *Infect. Immun.* 53:480–485.
156. Tsukamoto, M., T. Ochiya, S. Yoshida, T. Sugimura, and M. Terada. 1995. Gene transfer and expression in progeny after intravenous DNA injection into pregnant mice. *Nat. Genet.* 9:243–248.
157. Nabel, G. J., D. Gordon, D. K. Bishop, B. J. Nickoloff, Z. Y. Yang, A. Aruga, M. J. Cameron, E. G. Nabel, and A. E. Chang. 1996. Immune response in human melanoma after transfer of an allogeneic class I major histocompatibility complex gene with DNA-liposome complexes. *Proc. Natl. Acad. Sci U.S.A* 93:15388–15393.
158. Nabel, G. J., A. Chang, E. G. Nabel, G. E. Plautz, B. A. Fox, L. Huang, and S. Shu. 1992. Immunotherapy of malignancy by in vivo gene transfer therapy. *Hum. Gene Ther.* 3:399–410.

What we claim is:

1. A method of inhibiting the production of one or more inflammatory mediators comprising:
   A) administering an amphiphilic, polycationic compound, wherein said amphiphilic, polycationic compound comprises:
      a) a linear or branched, polymethylene or alkylamine, backbone and
      b) one or more lipophilic groups,
   B) allowing inhibition of said production of said inflammatory mediators.

2. A method of inhibiting the production of one or more inflammatory mediators as claimed in claim 1 wherein said backbone comprises two or more protonatable positively charged groups which are located at the termini of said backbone.

3. A method of inhibiting the production of one or more inflammatory mediators as claimed in claim 2 wherein said protonatable positively charged groups are independently selected from the group consisting of primary amino, imidazolinium, N,N'-unsubstituted amidinium, and N,N'-unsubstituted guanidium moieties.

4. A method of inhibiting the production of one or more inflammatory mediators as claimed in claim 1 wherein said lipophilic groups are derived from fatty acid or hydrocarbon substituents.

5. A method of inhibiting the production of one or more inflammatory mediators as claimed in claim 4 wherein the length of said fatty acid or hydrocarbon substitutents is not less than 6 carbon atoms and not greater than 24 carbon atoms.

6. A method of inhibiting the production of one or more inflammatory mediators as claimed in claim 1 wherein said lipophilic are attached to the backbone via amide, ester, carbamate, or urethane linkages.

7. A method of inhibiting the production of one or more inflammatory mediators as claimed in claim 1 wherein said amphiphilic, polycationic compound is selected from the group consisting of 1,3-di-oleoxyloxy-2-(6-carboxyspermyl)-propylamide; 2,3-dioleoxyloxy-N-[2(sperminecarboxamido)ethyl]-N,N-dimethyl-1-propanaminium; dioctadecylamidoglycylspermine; and pharmacologically suitable salt forms thereof.

8. A method of inhibiting the production of one or more inflammatory mediators as claimed in claim 7 wherein said amphiphilic, polycationic compound is 1,3-di-oleoxyloxy-2-(6-carboxyspermyl)-propylamide, either as free base, or in salt form.

9. A method of inhibiting the production of one or more inflammatory mediators as claimed in claim 7 wherein said amphiphilic, polycationic compound is 2,3-dioleoxyloxy-N-[2(sperminecarboxamido)ethyl]-N,N-dimethyl-1-propanaminium, either as free base, or in salt form.

10. A method of inhibiting the production of one or more inflammatory mediators as claimed in claim 7 wherein said amphiphilic, polycationic compound is dioctadecylamidoglycylspermine, either as free base, or in salt form.

11. A method of inhibiting the production of one or more inflammatory mediators as claimed in claim 1 wherein said inflammatory mediators are independently selected from the group consisting of tumor necrosis factor-$\alpha$, nitric oxide, interleukin-1$\beta$, interleukin-6, interleukin-8, interferon-$\beta$, interferon-$\gamma$, prostaglandins, leukotrienes, platelet activating factor, and procoagulant tissue factor.

12. A method of inhibiting the production of one or more inflammatory mediators as claimed in claim 11 wherein said inflammatory mediators are tumor necrosis factor-$\alpha$.

13. A method of inhibiting the production of one or more inflammatory mediators as claimed in claim 11 wherein said inflammatory mediators are interleukin-1 $\beta$.

14. A method of inhibiting the production of endothelial derived nitric oxide comprising:
A) administering an amphiphilic, polycationic compound, wherein said amphiphilic, polycationic compound comprises:
a) a linear or branched, polymethylene or alkylamine, backbone and
b) one or more lipophilic groups,
B) allowing inhibition of said production of said endothelial derived nitric oxide.

15. A method of inhibiting the production of endothelial derived nitric oxide as claimed in claim 14 wherein said backbone comprises two or more protonatable positively charged groups which are located at the termini of said backbone.

16. A method of inhibiting the production of endothelial derived nitric oxide as claimed in claim 15 wherein said protonatable positively charged groups are selected from the group consisting of primary amino, imidazolinium, N,N'-unsubstitued amidinium, and N,N'-unsubstituted guanidium moieties.

17. A method of inhibiting the production of endothelial derived nitric oxide as claimed in claim 14 wherein said lipophilic groups are derived from fatty acid or hydrocarbon substituents.

18. A method of inhibiting the production of endothelial derived nitric oxide as claimed in claim 14 wherein said lipophilic groups are attached to the backbone via amide, ester, carbamate, or urethane linkages.

19. A method of inhibiting the production of endothelial derived nitric oxide as claimed in claim 14 wherein said amphiphilic, polycationic compound is selected from the group consisting of 1,3-di-oleoxyloxy-2-(6-carboxyspermyl)-propylamide; 2,3-dioleoxyloxy-N-[2(sperminecarboxamido)ethyl]-N,N-dimethyl-1-propanaminium; dioctadecylamidoglycylspermine; and pharmacologically suitable salt forms thereof.

20. A method of inhibiting the production of endothelial derived nitric oxide as claimed in claim 19 wherein said said amphiphilic, polycationic compound is 1,3-di-oleoxyloxy-2-(6-carboxyspermyl)-propylamide, either as free base, or in salt form.

21. A method of inhibiting the production of endothelial derived nitric oxide as claimed in claim 19 wherein said amphiphilic, polycationic compound is 2,3-dioleoxyloxy-N-[2(sperminecarboxamido)ethyl]-N,N-dimethyl-1-propanaminium, either as free base, or in salt form.

22. A method of inhibiting the production of endothelial derived nitric oxide as claimed in claim 19 wherein said amphiphilic, polycationic compound dioctadecylamidoglycylspermine, either as free base, or in salt form.

23. A method of sequestering and thereby inhibiting the activity of lipopolysaccharide derived from Gram-negative bacteria, comprising:
A) administering an amphiphilic, polycationic compound, wherein said amphiphilic, polycationic compound comprises:
a) a linear or branched, polymethylene or alkylamine, backbone and
b) one or more lipophilic groups,
B) allowing inhibition of said activity of lipopolysaccharide derived from Gram-negative bacteria;
wherein said inflammatory mediators are independently selected from the group consisting of tumor necrosis factor-$\alpha$, nitric oxide, interleukin-1$\beta$, interleukin-6, interleukin-8, interferon-$\beta$, interferon-$\gamma$, prostaglandins, leukotrienes, platelet activating factor, and procoagulant tissue factor.

24. A method of sequestering and thereby inhibiting the activity of a lipopolysaccharide-like compound present in Gram-positive bacteria, comprising:
A) administering an amphiphilic, polycationic compound, wherein said amphiphilic, polycationic compound comprises:
a) a linear or branched, polymethylene or alkylamine, backbone and
b) one or more lipophilic groups,
B) allowing inhibition of said activity of a lipopolysaccharide-like compound present in Gram-positive bacteria;
wherein said inflammatory mediators are independently selected from the group consisting of tumor necrosis factor- α, nitric oxide, interleukin-1β, interleukin-6, interleukin-8, interferon-β, interferon-γ, prostaglandins, leukotrienes, platelet activating factor, and procoagulant tissue factor.

25. A method of enhancing treatment of Gram-negative sepsis and septic shock associated with Gram-negative septicemia, comprising:
   A) administering an amphiphilic, polycationic compound, wherein said amphiphilic, polycationic compound comprises:
      a) a linear or branched, polymethylene or alkylamine, backbone and
      b) one or more lipophilic groups.

26. A method of enhancing treatment of Gram-positive sepsis and septic shock associated with Gram-positive septicemia, comprising:
   A) administering an amphiphilic, polycationic compound, wherein said amphiphilic, polycationic compound comprises:
      a) a linear or branched, polymethylene or alkylamine, backbone and
      b) one or more lipophilic groups.

27. A method of enhancing systematic antibiotic use in Gram-negative infections or Gram-negative bacteremia in order to reduce or prevent pathological sequelae due to dysregulated production of one or more inflammatory mediators arising from antibiotic-induced release of endotoxins from Gram-negative bacteria, comprising:
   A) administering an amphiphilic, polycationic compound, wherein said amphiphilic, polycationic compound comprises:
      a) a linear or branched, polymethylene or alkylamine, backbone and
      b) one or more lipophilic groups,
   B) allowing inhibition of said production of said inflammatory mediators.

28. A method of enhancing systematic antibiotic use in Gram-positive infections or Gram-positive bacteremia in order to reduce or prevent pathological sequelae due to dysregulated production of one or more inflammatory mediators arising from antibiotic-induced release of lipopolysaccharide-like compounds from Gram-positive bacteria, comprising:
   A) administering an amphiphilic, polycationic compound, wherein said amphiphilic, polycationic compound comprises:
      a) a linear or branched, polymethylene or alkylamine, backbone and
      b) one or more lipophilic groups,
   B) allowing inhibition of said production of said inflammatory mediators.

* * * * *